(12) United States Patent
Giering et al.

(10) Patent No.: US 10,144,242 B2
(45) Date of Patent: Dec. 4, 2018

(54) METHOD FOR CHECKING A VALUE DOCUMENT, VALUE DOCUMENT, USE THEREOF, AND VALUE DOCUMENT SYSTEM

(71) Applicant: GIESECKE & DEVRIENT GMBH, Munich (DE)

(72) Inventors: Thomas Giering, Kirchseeon (DE); Johann Kecht, Munich (DE); Wolfgang Rauscher, Parkstetten (DE); Stephan Steinlein, Munich (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 67 days.

(21) Appl. No.: 14/432,260

(22) PCT Filed: Sep. 27, 2013

(86) PCT No.: PCT/EP2013/002918
§ 371 (c)(1),
(2) Date: Mar. 30, 2015

(87) PCT Pub. No.: WO2014/048577
PCT Pub. Date: Apr. 3, 2014

(65) Prior Publication Data
US 2015/0294522 A1 Oct. 15, 2015

(30) Foreign Application Priority Data
Sep. 28, 2012 (DE) .......... 10 2012 019 251

(51) Int. Cl.
*B42D 25/36* (2014.01)
*G07D 7/1205* (2016.01)
(Continued)

(52) U.S. Cl.
CPC .......... *B42D 25/36* (2014.10); *B42D 25/29* (2014.10); *G01N 21/6456* (2013.01);
(Continued)

(58) Field of Classification Search
None
See application file for complete search history.

(56) References Cited

U.S. PATENT DOCUMENTS 8,616,584 B2 12/2013 Scholz et al.
9,031,307 B2 5/2015 Giering
(Continued)

FOREIGN PATENT DOCUMENTS

DE 102005033598 A1 1/2007
DE 102008034021 A1 1/2010
(Continued)

OTHER PUBLICATIONS

International Preliminary Report on Patentability for corresponding International PCT Application No. PCT/EP2013/002918, dated Mar. 31, 2015.
(Continued)

*Primary Examiner* — Laura C Powers
(74) *Attorney, Agent, or Firm* — Workman Nydegger

(57) ABSTRACT

A method for checking the authenticity and/or the nominal value of a value document having luminescent feature substances, comprises: a1) the step of carrying out a location-specific measurement of first luminescence intensities (L1) at a first emission wavelength at different locations of the value document that have the location coordinates (O), to thereby obtain (O/L1) measurement value pairs; b1) the step of statistically analyzing the first luminescence intensities (L1) measured in dependence on the individual location coordinates (O), by determining at least one statistical parameter using a statistical method; and c1) the step of comparing the statistical parameter determined in the step b1) with one or more threshold values.

3 Claims, 13 Drawing Sheets

(51) Int. Cl.
  *B42D 25/29* (2014.01)
  *G01N 21/84* (2006.01)
  *G01N 21/64* (2006.01)
  *G07D 7/12* (2016.01)
  *G07D 7/00* (2016.01)
(52) U.S. Cl.
  CPC .............. *G01N 21/84* (2013.01); *G07D 7/00* (2013.01); *G07D 7/12* (2013.01); *G07D 7/1205* (2017.05)

(56) References Cited

U.S. PATENT DOCUMENTS

| | | | |
|---|---|---|---|
| 2002/0066543 A1* | 6/2002 | Lilly | B41M 3/144 162/140 |
| 2007/0189595 A1 | 8/2007 | Giering | |
| 2007/0257118 A1* | 11/2007 | Riley | G06K 1/121 235/494 |
| 2009/0051158 A1 | 2/2009 | Scholz et al. | |
| 2010/0084852 A1* | 4/2010 | Hampden-Smith | C09D 11/322 283/92 |
| 2010/0155679 A1 | 6/2010 | Olm et al. | |

FOREIGN PATENT DOCUMENTS

| | | |
|---|---|---|
| EP | 0947964 A1 | 10/1999 |
| WO | 2005036481 A1 | 4/2005 |

OTHER PUBLICATIONS

International Search Report for corresponding International PCT Application No. PCT/EP2013/002918, dated Jan. 3, 2014.

\* cited by examiner

Random distribution, 28000 particles

METHOD FOR CHECKING A VALUE DOCUMENT, VALUE DOCUMENT, USE THEREOF, AND VALUE DOCUMENT SYSTEM

FIELD OF THE INVENTION

Background

This invention relates to a method for checking, in particular the authenticity and/or the nominal value of, a value document having luminescent feature substances. The invention relates further to value documents that are adapted to the checking method, and their use in the method. The invention relates furthermore to value-document systems having value documents of different nominal values or currencies.

Safeguarding the authenticity of value documents by means of luminescent substances has been known for some time. Preferably, host lattices doped with rare earth metals are used, with the absorption and emission regions being variable within a broad range through suitable coordination of rare earth metal and host lattice. The use of magnetic and electrically conductive materials for safeguarding authenticity is also known. Magnetism, electrical conductivity and luminescence emission are detectable by machine using commercially available measuring instruments, while luminescence with emission in the visible region in sufficient intensity is also detectable visually.

WO 2005/036481 A1 describes an apparatus and a method for checking value documents having luminescent feature substances. Carrying out the evaluation of the captured luminescence radiation on the basis of an integrated luminescence measurement, i.e. integrating the measured luminescence radiation of a track extending across the value document, makes it possible to capture and distinguish weakly luminous feature substances especially easily.

DE 10 2005 033 598 A1 discloses a sheet-shaped value document having luminescent feature substances and the production and check of such a value document. The value document described therein contains a luminescent feature substance which is present both with low concentration over the full area and with higher concentration in certain partial areas.

DETAILED DESCRIPTION OF VARIOUS EMBODIMENTS

Starting out from the hereinabove cited prior art, the present invention is based on the object of providing a value document with improved anti-forgery security as well as a method for checking the presence thereof.

SUMMARY OF THE INVENTION 1. (First aspect) A method for checking, in particular the authenticity and/or the nominal value of, a value document having luminescent feature substances, comprising:

a1) the step of carrying out a location-specific measurement of first luminescence intensities (L1) at a first emission wavelength at different locations of the value document that have the location coordinates (O), to thereby obtain (O/L1) measurement value pairs;

b1) the step of statistically analyzing the first luminescence intensities (L1) measured in dependence on the individual location coordinates (O), by determining at least one statistical parameter using a statistical method; and c1) the step of comparing the statistical parameter determined in the step b1) with one or more threshold values.

The step c1) is in particular the step of checking whether the statistical parameter determined in the step b1) lies above or below a certain limiting value, or whether the statistical parameter determined in the step b1) lies within a range that is formed by a lower limiting value and an upper limiting value.

1a. (First aspect—variant of item 1) A method for checking, in particular the authenticity and/or the nominal value of, a value document having non-luminescent feature substances, comprising:

a1) the step of carrying out a location-specific measurement of first measurement signal intensities (L1) at different locations of the value document that have the location coordinates (O), to thereby obtain (O/L1) measurement value pairs;

b1) the step of statistically analyzing the first measurement signal intensities (L1) measured in dependence on the individual location coordinates (O), by determining at least one statistical parameter using a statistical method; and c1) the step of comparing the statistical parameter determined in the step b1) with one or more threshold values.

The step c1) is in particular the step of checking whether the statistical parameter determined in the step b1) lies above or below a certain limiting value, or whether the statistical parameter determined in the step b1) lies within a range that is formed by a lower limiting value and an upper limiting value. The non-luminescent feature substance can be in particular a substance detectable by means of nuclear resonance spectroscopy, electron spin resonance spectroscopy, nuclear quadrupole resonance spectroscopy, SER (surface enhanced Raman) spectroscopy or SEIRA (surface enhanced infrared absorption) spectroscopy.

2. (preferred) The method according to item 1, wherein the statistical method and the statistical parameter are chosen from the methods and parameters of the field of descriptive statistics or of numerical classification methods, with the field of descriptive statistics being preferred and therein in particular the field of dispersion measures being preferred, and with the field of numerical classification methods likewise being preferred, and therein in particular an application to frequency distribution data and/or frequency domains being preferred.

3. (preferred) The method according to item 1, wherein at least 20, preferably at least 40, particularly preferably at least 100, (O/L1) measurement value pairs are evaluated per value document for determining the statistical parameter.

4. (preferred) The method according to any of items 1 to 3, wherein the luminescence intensities drawn on for the statistical analyzing step are respectively corrected luminescence intensities converted by means of an algorithm.

5. (preferred) The method according to item 4, wherein the value document has an additional, luminescent feature substance suitable as a normalizing substance, so that effects influencing the measurement of the luminescence intensities, such as e.g. an attenuation of measured luminescence intensities through partial overprinting of the value document, are correctable on the basis of the measured luminescence intensity of the normalizing substance.

6. (preferred) The method according to any of items 1 to 5, wherein the luminescence intensities stated in the step b1) form a bimodal frequency distribution, i.e. in a histogram plotting relative frequency as a function of intensity the frequency distribution has the form of altogether two peaks with exactly two maxima.

6a. (preferred—variant of item 6) The method according to item 1a, wherein the measurement signal intensities stated in the step b1) form a bimodal frequency distribution, i.e. in a histogram plotting relative frequency as a function of intensity the frequency distribution has the form of altogether two peaks with exactly two maxima.

7. (preferred) The method according to any of items 1 to 5, wherein:

the luminescence intensities stated in the step b1) form a multimodal or polymodal frequency distribution, i.e. in a histogram plotting relative frequency as a function of intensity the frequency distribution has the form of a plurality (n) of peaks with exactly (n) maxima, where n≥3.

7a. (preferred—variant of item 7) The method according to item 1a, wherein:

the measurement signal intensities stated in the step b1) form a multimodal or polymodal frequency distribution, i.e. in a histogram plotting relative frequency as a function of intensity the frequency distribution has the form of a plurality (n) of peaks with exactly (n) maxima, where n≥3.

8. (Second aspect) A value document which is adapted to the method for checking, in particular its authenticity and/or its nominal value, according to item 1 or 6, wherein:

the value document has first luminescent particles which emit at a first emission wavelength;

the first luminescent particles are formed with bimodal size distribution, i.e. with two mutually delimited, certain sizes; and the first luminescent particles are present in the value document in homogeneous distribution.

The formulation "luminescent particles formed with two mutually delimited, certain sizes" means in particular that in the histogram of grain size distribution (see FIG. 26, plot of relative frequency as a function of grain size) two separate maxima or peaks are present that are mutually different, i.e. not identical. An overlap of the two peaks may partly be present, i.e. the two peaks do not have to be 100% mutually separate.

8a. (Second aspect—variant of item 8) A value document which is adapted to the method for checking, in particular its authenticity and/or its nominal value, according to item 1a or 6a, wherein:

the value document has first non-luminescent particles;

the first non-luminescent particles are formed with bimodal size distribution, i.e. with two mutually delimited, certain sizes; and the first non-luminescent particles are present in the value document in homogeneous distribution. The first non-luminescent particles can be chosen in particular from the group consisting of substances detectable by means of nuclear resonance spectroscopy, electron spin resonance spectroscopy, nuclear quadrupole resonance spectroscopy, SER (surface enhanced Raman) spectroscopy or SEIRA (surface enhanced infrared absorption) spectroscopy.

9. (preferred) The value document according to item 8, wherein the bimodal size distribution in the histogram is so configured that one maximum is one and a half to 50 times, preferably 2 to 20 times, particularly preferably 4 to 10 times, greater with regard to its grain size than the other maximum.

10. (preferred) The value document according to either of items 8 to 9, wherein the bimodal size distribution is produced by a mixture of smaller particles and larger single crystals.

11. (preferred) The value document according to either of items 8 to 9, wherein the bimodal size distribution is produced by a mixture of smaller particles and larger particles, and the larger particles are luminescent, particulate agglomerates of a solid homogeneous phase of a luminophore.

12. (Third aspect) A value document which is adapted to the method for checking, in particular its authenticity and/or its nominal value, according to item 1 or 7, wherein:

the value document has first luminescent particles which emit at a first emission wavelength;

the first luminescent particles are formed with multimodal size distribution, i.e. with at least three mutually delimited, certain sizes; and the first luminescent particles are present in the value document in homogeneous distribution.

12a. (Third aspect—variant of item 12) A value document which is adapted to the method for checking, in particular its authenticity and/or its nominal value, according to item 1a or 7a, wherein:

the value document has first non-luminescent particles;

the first non-luminescent particles are formed with multimodal size distribution, i.e. with at least three mutually delimited, certain sizes; and the first non-luminescent particles are present in the value document in homogeneous distribution. The first non-luminescent particles can be chosen in particular from the group consisting of substances detectable by means of nuclear resonance spectroscopy, electron spin resonance spectroscopy, nuclear quadrupole resonance spectroscopy, SER (surface enhanced Raman) spectroscopy or SEIRA (surface enhanced infrared absorption) spectroscopy.

13. (preferred) The value document according to any of items 8 to 12, wherein the grain size (D99) of the luminescent particles is smaller than 30 µm, preferably smaller than 20 µm.

14. (Fourth aspect) Use of the value document according to item 8 in the method according to item 1 or 6.

15. (Fifth aspect) Use of the value document according to item 12 in the method according to item 1 or 7.

16. (Sixth aspect) A value-document system, comprising value documents with a first nominal value or a first currency (the so-called first group of value documents), value documents with a second nominal value or a second currency (so-called second group of value documents) and value documents with a third nominal value or a third currency (so-called third group of value documents), wherein at least two of the three groups of value documents are chosen from the following three kinds of value documents, and preferably all three groups of value documents are represented by the following three kinds of value documents:

first value documents, wherein each value document has first luminescent particles which emit at a first emission wavelength, and the first luminescent particles are present in the value document in homogeneous distribution, and the first luminescent particles are formed with unimodal grain size distribution, i.e. with a certain grain size, and the first luminescent particles are in particular luminescent, particulate agglomerates of a solid homogeneous phase of a luminophore;

second value documents which are respectively defined according to item 8, wherein each value document possesses the luminescent particles in a bimodal grain size distribution; and third value documents which are respectively defined according to item 12, wherein each value document possesses the luminescent particles in a multimodal grain size distribution.

17. (preferred) The value-document system according to item 16, wherein the concentrations of the luminescent particles in the respective first, second and third value documents are so chosen that the luminescent particles with a first grain size distribution that possess a higher luminescence intensity than luminescent particles with a second grain size distribution are used in a lower concentration, wherein preferably the concentrations of the luminescent particles in the corresponding value documents are so chosen that all value documents have the same average luminescence intensity.

18. (preferred) The value-document system according to item 16 or 17, wherein at least in one group of value documents the luminescent particles are formed completely or partly by luminescent, particulate agglomerates of a solid homogeneous phase of a luminophore.

19. (preferred) The value-document system according to any of items 16 to 18, which comprises in addition to the stated groups of value documents further groups of value documents which are respectively chosen from first, second or third kinds of value documents, with groups of value documents of the same respective kind of value documents mutually differing in the position of at least one maximum of the grain size distribution of the contained luminescent particles.

20. (preferred) The value-document system according to any of items 16 to 19, wherein the value documents contain in addition to the stated luminescent particles further luminophores with different spectral properties, preferably further luminescent particles with different emission.

DETAILED DESCRIPTION OF THE INVENTION

Figure 1:
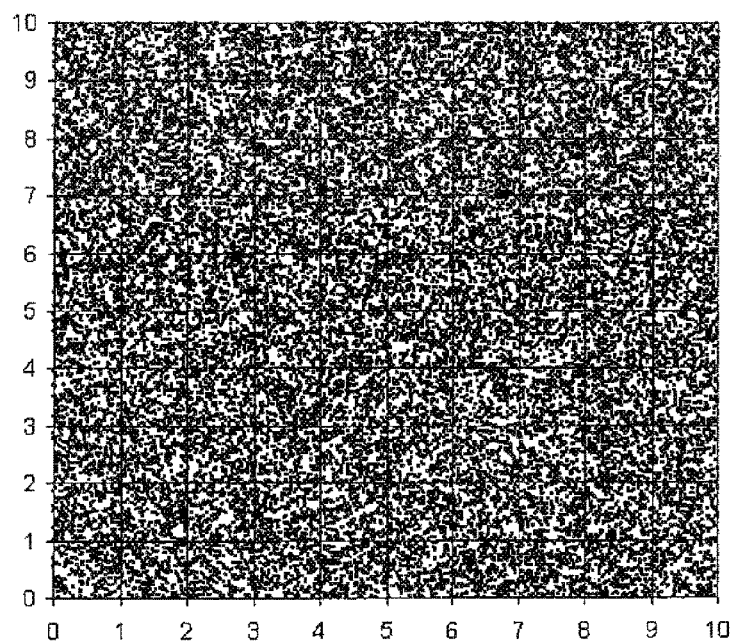
FIG. 1 shows a random distribution of 2,800 luminophore particles in a field with a relative luminance of 0.1 in a 10×10 field.

The terms frequency distribution, parameter, variance, standard deviation, histogram, relative frequency, mode or modal value or peak, unimodal (frequency) distribution, bimodal (frequency) distribution are known in the literature (see e.g.: E. Hering, R. Martin, M. Stohrer "Physik für Ingenieure", VDI-Verlag GmbH, 3rd ed. 1989, chapter 1.3.2. "Messgenauigkeit"; K. Ulshöfer, H. Hornschuh "Mathematische Formelsammlung", Verlag Konrad Wittwer Stuttgart, 1984, chapter 6.1 "Beschreibende Statistik, Datenerhebung"; Wikipedia (as on 21 Sep. 2012)—The free encyclopedia: http://de.wikipedia.org/wiki/Bimodale_Verteilung).

For statistically analyzing the location-dependent luminescence data, different mathematical methods can be used. Hereinafter some preferred statistical methods and parameters that are especially suitable for this purpose will be stated.

Preferably, an evaluation of the location-dependent luminescence data is effected with methods of descriptive statistics. A bank note is for example rasterized into pixels, or measured at a plurality of randomly selected places, and one or more of the following parameters from the field of descriptive statistics is computed from the resultant data. Said parameters are then compared with threshold values, for sorting or authenticating the bank notes. A threshold value (alternatively also designated a threshold or limiting value) designates here a certain absolute or relative numerical value upon whose exceeding or undershooting a different assignment in the classification of the value document is performed, for example the distinguishing of authentic/false value documents or the assignment to different denominations and/or currencies.

Descriptive statistics divides parameters, inter alia, into location measures such as mean, median and quantile, as well as dispersion measures such as standard deviation, average absolute deviation and interquartile range. Preferably, at least one parameter from the area of dispersion measures is used for rating the location-dependent luminescence data. Preferably, intensity-corrected dispersion measures are used, that is to say, the dispersion measures are normalized or corrected with the aid of location measures.

A further area of descriptive statistics is shape measures such as the skewness and quartile skewness of a distribution. These are preferably used for analyzing luminescence intensity distributions that have a right or left skewness. Such distributions can be produced for example by using right- or left-skewed unimodal or bimodal or multimodal grain size distributions of luminophores. Further, general measures of descriptive statistics can be used, for example i central moment $E((X-\mu)^k)$, which describes for k=2 the variance, for k=3 the skewness and for k=4 the kurtosis of a distribution.

Alternatively or in addition to the just described methods of descriptive statistics, methods from the area of numerical classification methods are preferably used, these preferably being applied to frequency distribution data. For this purpose, a bank note is for example rasterized into pixels, or measured at a plurality of randomly selected places, and the resultant intensity values divided into n frequency classes, so that a frequency vector as an n-tuple is obtained for each bank note. Said vector corresponds to a point in n-dimensional space $R^n$. The point clouds in said space that are thus obtained for a multiplicity of notes can be rated especially advantageously with numerical classification methods in order to assign the bank notes to different classifications such as authentic/false or different denominations and/or currencies. Examples of suitable numerical classification methods are statistical classification, nearest-neighbor classification, quadratic classification, polynomial classifier, support vector machines (SVM), and neural networks.

Further reading on the above topic:
(1) H. Niemann: "Klassifikation von Mustern", Springer-Verlag, Berlin 1983, ISBN 3-540-12642-2, pages 159-261, as well as extended on-line version, pages 303-481, available under (as on 21 Sep. 2012): http://www5.informatik.uni-erlangen.de/fileadmin/Persons/NiemannHeinrich/klassifikation-von-mustern/m001links.html
(2) Software "Mathematica" from the company Wolfram Research.

Further information on the above topic is available on the Internet (as on: 21 Sep. 2012) on the following pages:
http://en.wikipedia.org/wiki/Descriptive_statistics
http://de.wikipedia.org/wiki/Dispersionsmasse
http://de.wikipedia.org/wiki/Schiefe_(Statistik)

Value documents within the framework of this invention are objects such as bank notes, checks, shares, value stamps, identity cards, passports, credit cards, deeds and other documents, labels, seals, and objects to be authenticated such as for example CDs, packages and the like. The preferred area of application is bank notes which are in particular based on a paper substrate.

Luminescent substances (also designated as luminophores herein) are standardly used for authenticating bank notes. In the case of a luminescent authentication feature which is e.g. incorporated in the paper of a bank note at different places, the luminescence signals of the feature are naturally subject to certain variations at the different places. The present invention is based on the finding that the statistical fluctuation of the spatial signal intensity distribution can be influenced in a targeted manner by choosing suitable factors, e.g. by adjusting certain grain size distributions of the luminescent authentication feature. Grain size distributions are preferably chosen here that are not obtainable or only with difficulty, by means of a conventional grinding or production process. Suitable grain size distributions are e.g.

luminescent particles with unimodal size distribution which are in particular narrowly particle size distributed and in particular possess grain sizes (D99) between 10 μm and 30 μm;

luminescent particles with bimodal grain size distribution, i.e. besides a first species with a diameter $d_{m1}$ a second species with a diameter $d_{m2}$ is present, where $d_{m1} < d_{m2}$.

The luminescent particles can be based e.g. on a matrix-forming inorganic solid which is doped with one or more rare earth metals or transition metals.

Suitable inorganic solids that are suitable for forming a matrix are for example:

oxides, in particular tri- and tetravalent oxides such as e.g. titanium oxide, aluminum oxide, iron oxide, boron oxide, yttrium oxide, cerium oxide, zirconium oxide, bismuth oxide, as well as more complex oxides such as e.g. garnets, including e.g. yttrium iron garnets, yttrium aluminum garnets, gadolinium gallium garnets;

perovskites, including yttrium aluminum perovskite, lanthanum gallium perovskite; spinels, including zinc aluminum spinels, magnesium aluminum spinels, manganese iron spinels; or mixed oxides such as e.g. ITO (indium tin oxide);

oxyhalides and oxychalcogenides, in particular oxychlorides such as e.g. yttrium oxychloride, lanthanum oxychloride; as well as oxysulfides, such as e.g. yttrium oxysulfide, gadolinium oxysulfide;

sulfides and other chalcogenides, e.g. zinc sulfide, cadmium sulfide, zinc selenide, cadmium selenide;

sulfates, in particular barium sulfate and strontium sulfate;

phosphates, in particular barium phosphate, strontium phosphate, calcium phosphate, yttrium phosphate, lanthanum phosphate, as well as more complex phosphate-based compounds such as e.g. apatites, including calcium hydroxyl apatites, calcium fluorapatites, calcium chlorapatites; or spodiosites, including e.g. calcium fluorospodiosites, calcium chlorospodiosites;

silicates and aluminosilicates, in particular zeolites such as e.g. zeolite A, zeolite Y; zeolite-related compounds such as e.g. sodalites; feldspars such as e.g. alkali feldspars, plagioclases;

further inorganic compound classes such as e.g. vanadates, germanates, arsenates, niobates, tantalates.

It is preferred to use luminescent particles that emit in the non-visible spectrum, i.e. in the UV or NIR region (the abbreviation "NIR" designating the term "near infrared"). With regard to the incorporation of the luminescent particles into value documents, e.g. bank notes, it is preferred that the particles have a maximum grain size of 30 μm, particularly preferably a maximum grain size of 20 μm.

The principle underlying the invention will be described in detail hereinafter in connection with FIGS. 1 to 6 with reference to a first preferred embodiment.

First Preferred Embodiment

The authentication of a luminescent authentication feature is conventionally effected by means of suitable sensors which detect the luminescence at at least one location, normally at a plurality of locations, of the value document through excitation with light of a suitable wavelength. With regard to a correct recognition and assessment of authenticity it would be desirable to measure a constant luminescence signal at all potential measurement points of the value document, e.g. to detect a homogeneous luminescence signal over the total paper body of a bank note. This is promoted, inter alia, by a high luminophore concentration and a large measuring area, since a high number of luminophore particles is captured upon each measurement here and thus a good averaging arises.

In contrast, it is customary to use as small amounts of feature substance as possible for reasons of security and cost. Thus, a relatively low concentration of luminophore particles prevails. The minimal amount to be incorporated depends on, inter alia, the efficiency and luminance of the feature substance, so that particularly the highly efficient feature substances most suitable for safeguarding are used in especially low concentration. Likewise, it is often more advantageous in terms of measuring technology to obtain the excitation by intense irradiation of a small measurement spot, instead of exciting over a large area with low intensity. The combination of low luminophore concentration and small measuring region promotes an elevated statistical fluctuation of the measurement signal. FIGS. 1 to 6 show this relation schematically.

FIGS. 1 to 6 show the use of three different luminophore particle classes which have a different luminance per particle. The different luminance can be based here e.g. on different particle sizes or on a change of chemical composition, such as e.g. of dopant concentration. For the sake of simplicity it has been assumed here that all luminophore particles of a respective class are homogeneous, i.e. all luminophore particles have the same size and an identical composition.

Figure 2:
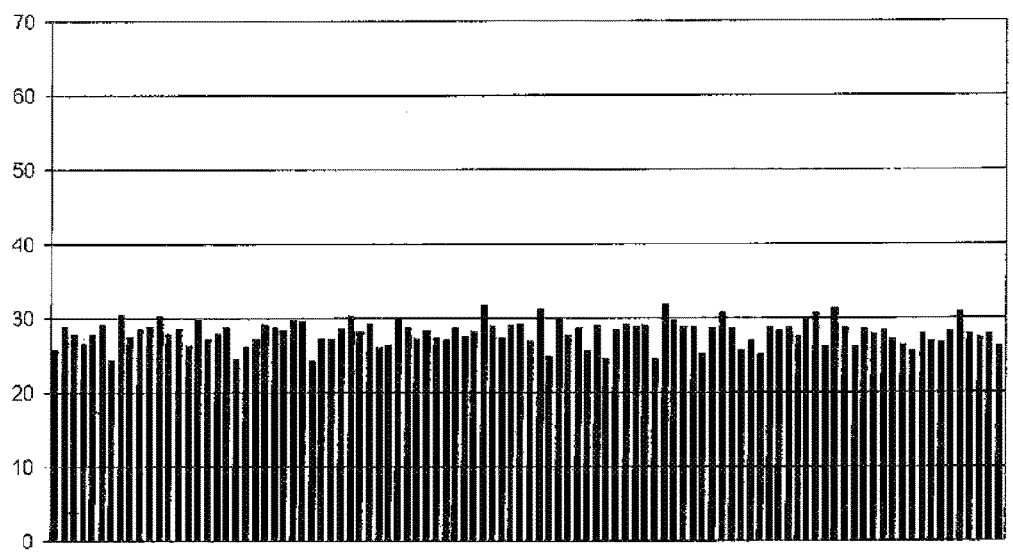
FIG. 2 shows a measured luminescence intensity for the field of FIG. 1.

FIG. 1 shows the random distribution of 28,000 luminophore particles with a relative luminance of 0.1 in a 10×10 field. FIG. 2 shows the resultant luminescence signal (i.e. the measured luminescence intensity) for each of the fields 1 to 10 (Y-axis) in the rows 1 to 10 (X-axis).

Figure 3:
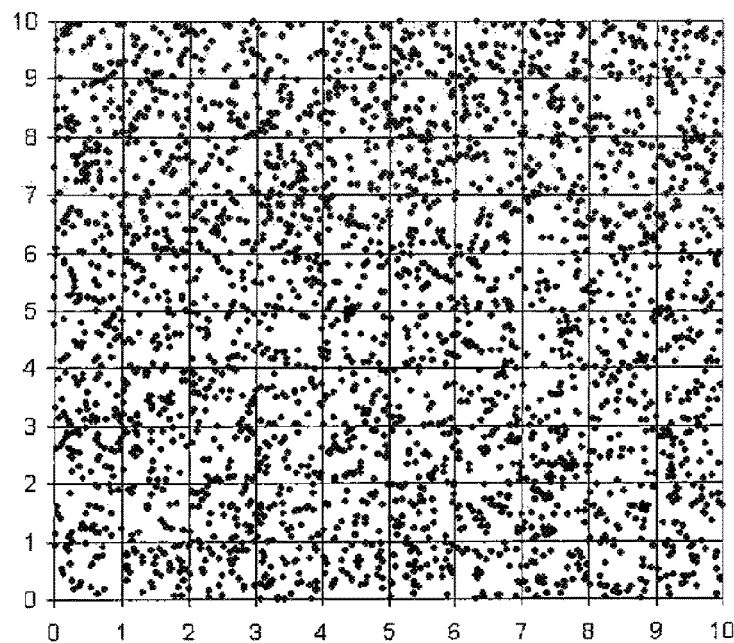
FIG. 3 shows a random distribution of 2,800 luminophore particles in a field with a relative luminance of 1.0 in a 10×10 field.
Figure 4:
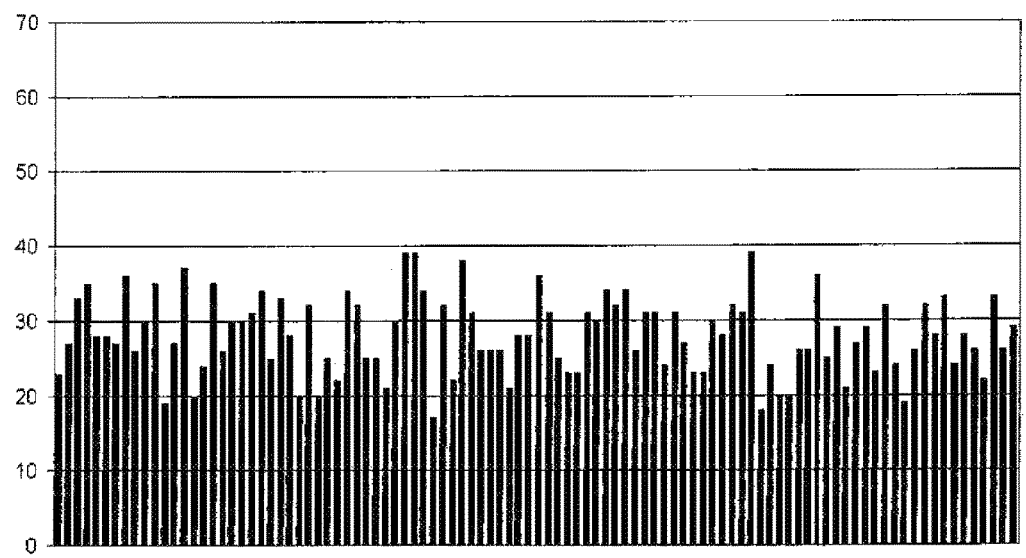
FIG. 4 shows a measured luminescence intensity for the field of FIG. 3.

FIG. 3 shows the random distribution of 2,800 luminophore particles with a relative luminance of 1.0 in a 10×10 field. FIG. 4 shows the resultant luminescence signal (i.e. the measured luminescence intensity) for each of the fields 1 to 10 (Y-axis) in the rows 1 to 10 (X-axis).

Figure 5:
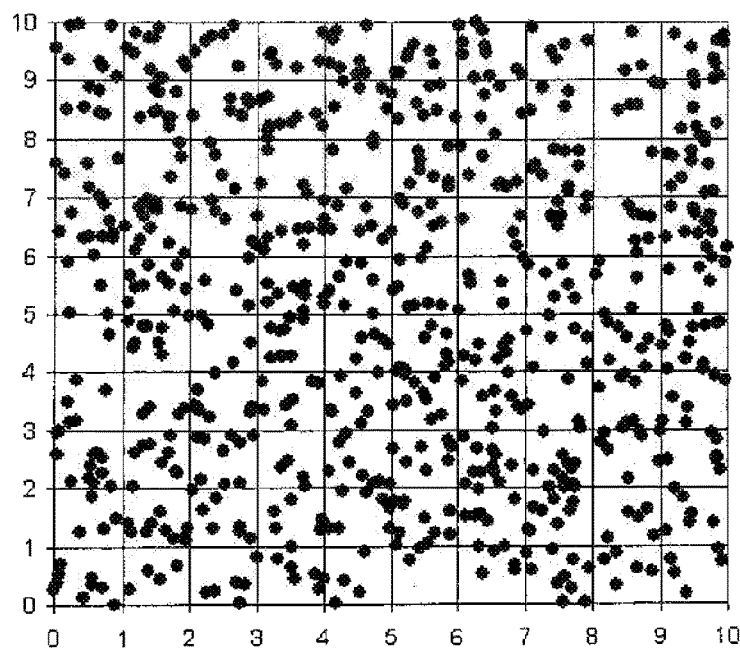
FIG. 5 shows a random distribution of 700 luminophore particles in a field with a relative luminance of 4.0 in a 10×10 field.
Figure 6:
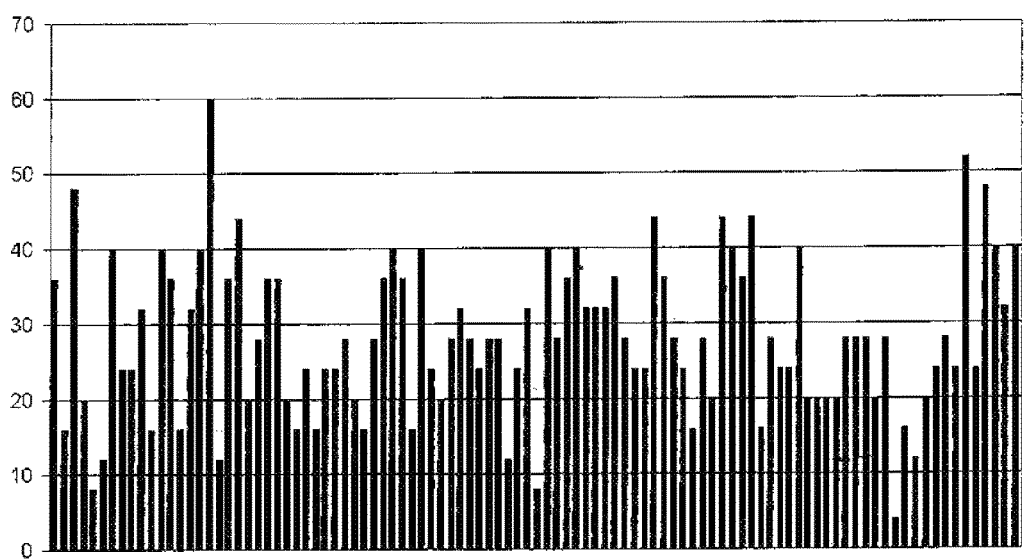
FIG. 6 shows a measured luminescence intensity for the field of FIG. 5.

FIG. 5 shows the random distribution of 700 luminophore particles with a relative luminance of 4.0 in a 10×10 field. FIG. 6 shows the resultant luminescence signal (i.e. the measured luminescence intensity) for each of the fields 1 to 10 (Y-axis) in the rows 1 to 10 (X-axis).

To obtain an, on average, equally strong signal in all three cases, a different number of particles must respectively be used. The very homogeneous signal distribution obtained upon the use of many, weakly luminous particles (see FIG. 2) begins to fluctuate more and more strongly in the course of the transition to few, more intensely luminous particles (see FIGS. 4 and 6).

Due to the described differences in the statistical signal fluctuation it is possible to mutually distinguish value-document classes in which different luminophore particle classes are employed, even in the case of otherwise identical spectral properties, such as e.g. the luminescence band position, the excitation spectrum and the decay time, e.g. via an analysis of the distribution and height of the deviations from the signal mean.

With reference to the following exemplary embodiment 1 the hereinabove explained, first preferred embodiment will be described more closely.

Exemplary Embodiment 1

Starting out from a rare earth-doped luminescent pigment based on YAG and having an average grain size (A2), there are produced by grinding in an agitator ball mill a finer pigment (A1) as well as, by controlled agglomeration, a coarser pigment (A3) (see Table 1).

TABLE 1

Grain sizes (the terms D50, D90 and D99 designating that 50%, 90% and 99% of the particles of a grain size distribution have grain sizes that are smaller than or equal to the stated value)

| Designation | D50 [µm] | D90 [µm] | D99 [µm] |
|---|---|---|---|
| A1 | 0.3 | 1.4 | 2.2 |
| A2 | 2.4 | 7 | 11.4 |
| A3 | 11 | 17 | 20 |

Figure 7:
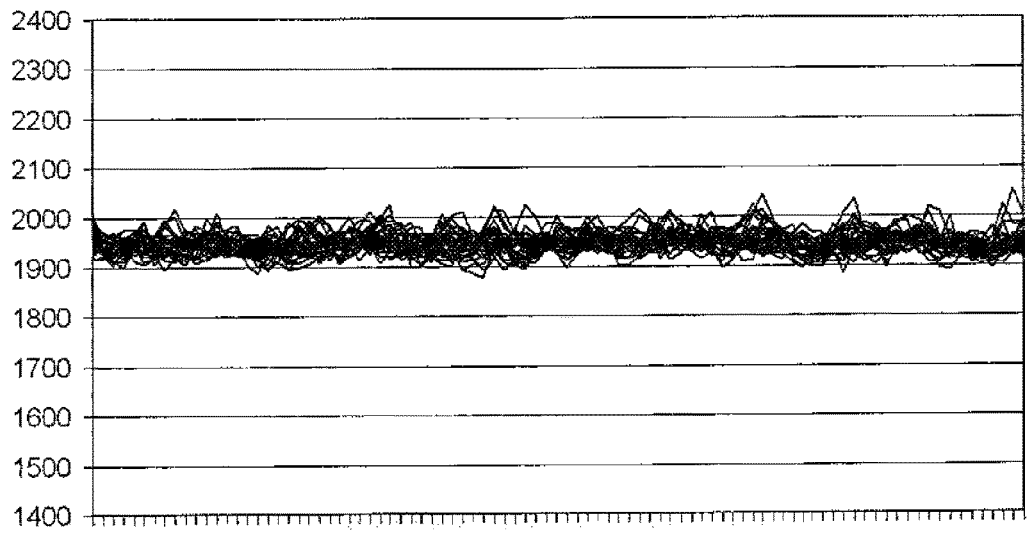
FIG. 7 shows a measurement signal of a sheet with a fine pigment (A1)
Figure 9:
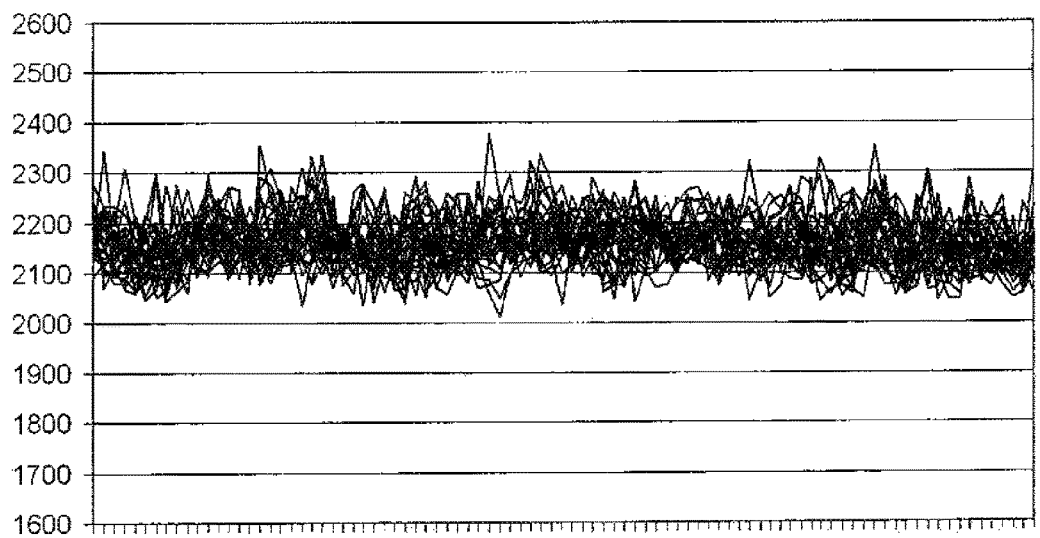
FIG. 9 shows a measurement signal of a sheet with an average pigment (A2)
Figure 11:
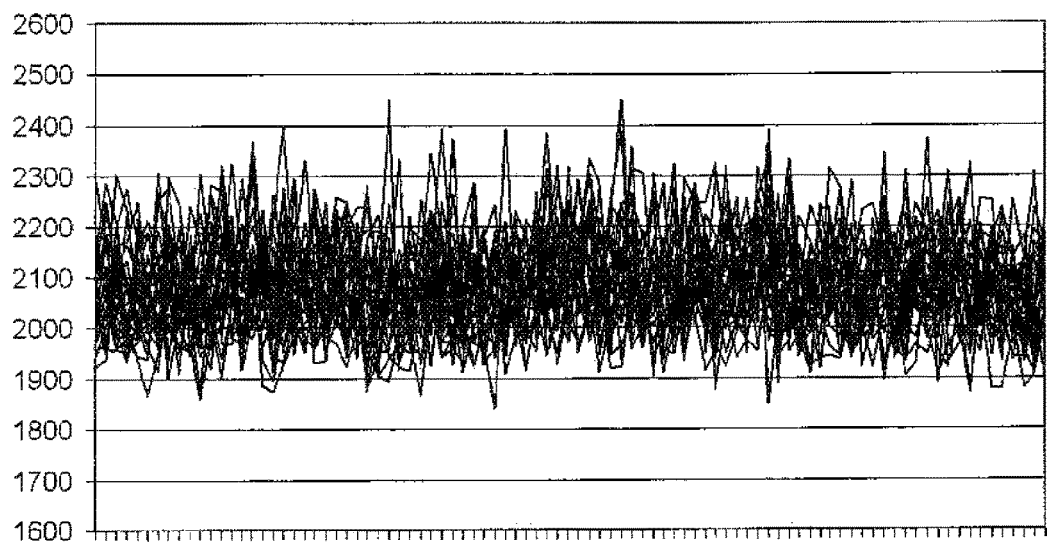
FIG. 11 shows a measurement signal of a sheet with a coarse pigment (A3)

Subsequently there was produced in a sheet former a sheet of paper in each case, with 2 per mill (A1) and 1 per mill (A2, A3) weight fraction of feature substance being contained per sheet. The sheets containing the feature were thereafter measured by means of a sensor. FIGS. 7, 9 and 11 show the measurement signals of the sheets. A plurality of measurement points at different places of the sheet were measured, and the ascertained measurement signals of consecutive measurement points were connected with a line (measurement series). FIGS. 7, 9 and 11 respectively show the superimposition of a multiplicity of such measurement series.

Figure 8:
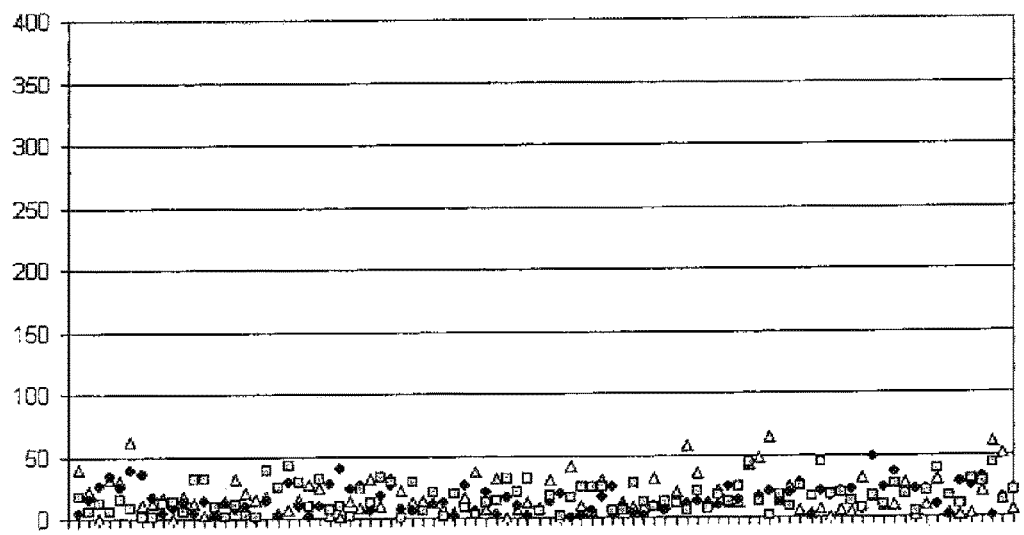
FIG. 8 shows an absolute value of the difference of a measurement signal over a preceding measurement signal for three randomly chosen individual measurements of FIG. 7.
Figure 10:
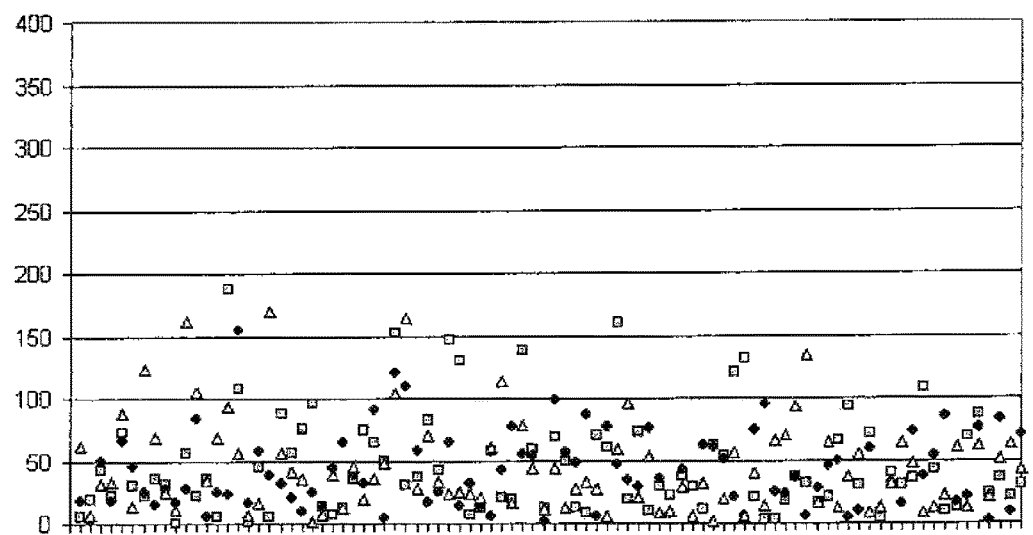
FIG. 10 shows an absolute value of the difference of a measurement signal over a preceding measurement signal for three randomly chosen individual measurements of FIG. 9.
Figure 12:
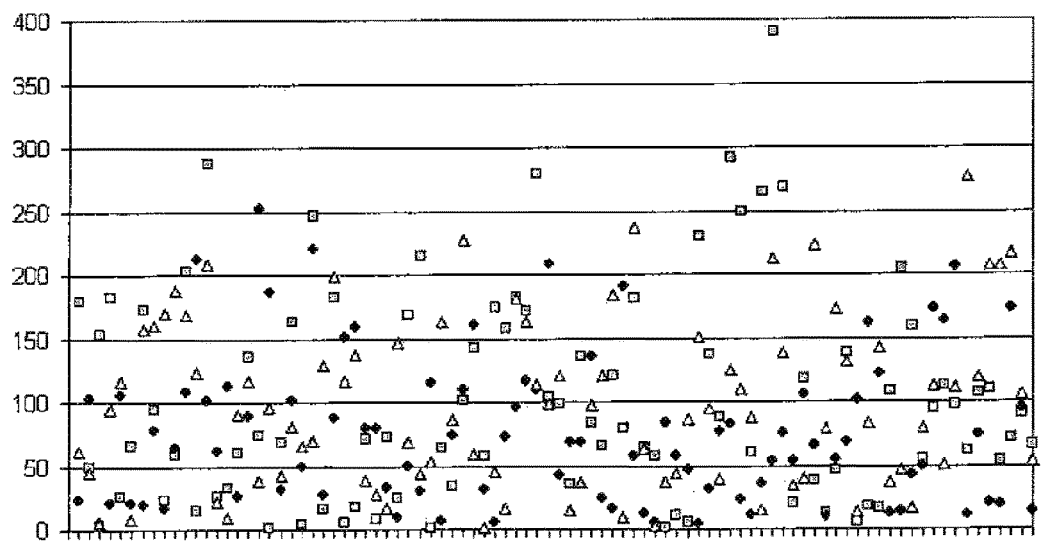
FIG. 12 shows an absolute value of the difference of a measurement signal over a preceding measurement singal for three randomly chosen individual measurements of FIG. 11.

Additionally, in FIGS. 8, 10 and 12 the absolute value of the difference of a measurement signal over the preceding measurement signal is respectively plotted for three randomly chosen individual measurement series in each case. The three different measurement series respectively bear different symbols so as to be better distinguished: white triangles, gray squares and black circles.

A parameter for the fluctuation of the measurement signal is e.g. the mean of the absolute values of said differences upon measurement of measurement series with 90 measurement points. Clear differences result here for the respective samples, there being respectively stated hereinafter the mean of the parameter followed by its standard deviation between a plurality of measurement series: A1 (mean: 16±2); A2 (mean: 45±4); A3 (mean: 96±8).

Second Preferred Embodiment

A second preferred embodiment is based on mixing different particle classes with different luminosities. Thus, e.g. a luminescent authentication feature with a bimodal, or in general multimodal, particle size distribution produces a completely different kind of signal fluctuation compared to corresponding unimodal distributions (see FIGS. 13, 14, 26 and 27).

Figure 13:
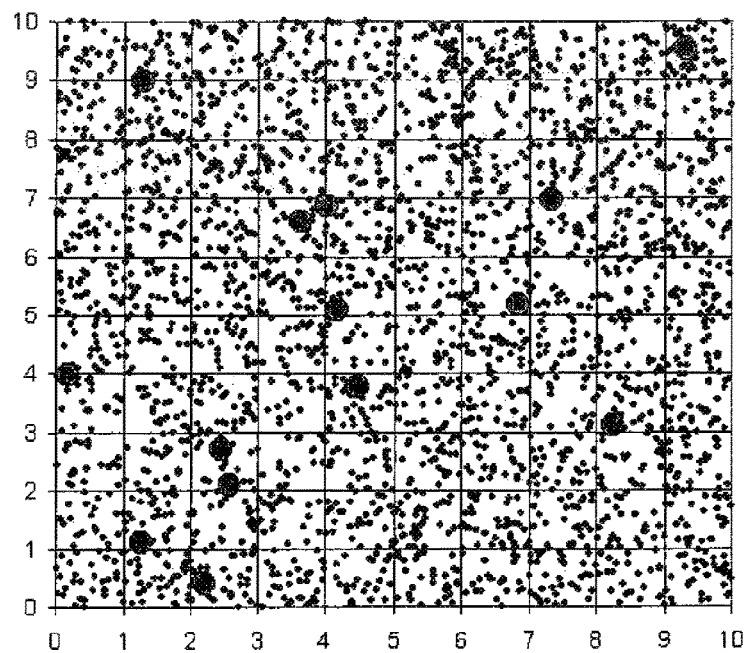
FIG. 13 shows a random distribution of 2,800 luminophore particles with a relative luminance of 1.0 and 14 particles with a relative luminescence of 100, in a 10×10 field.
Figure 14:
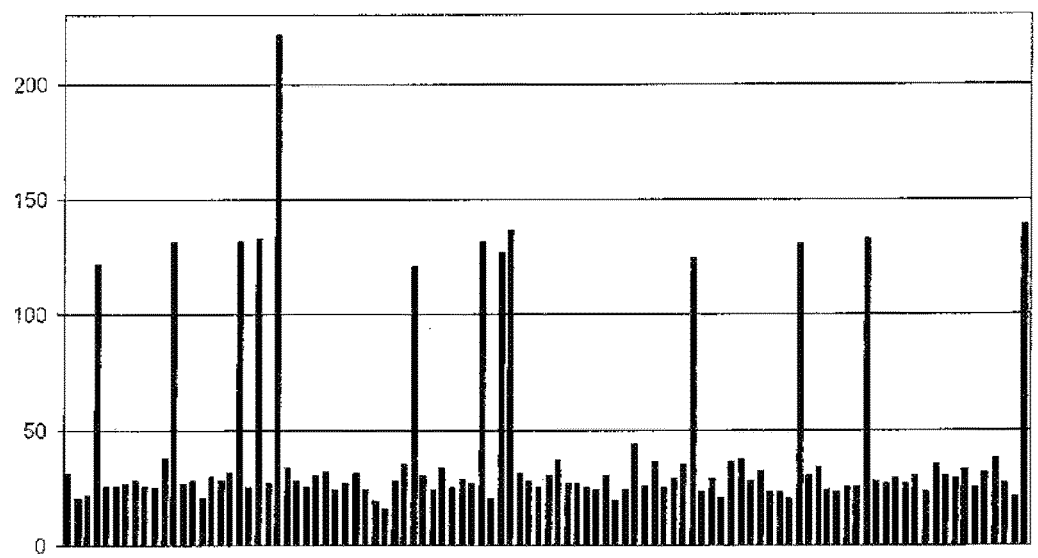
FIG. 14 shows a measured luminescence intensity for the field of FIG. 13.
Figure 15:
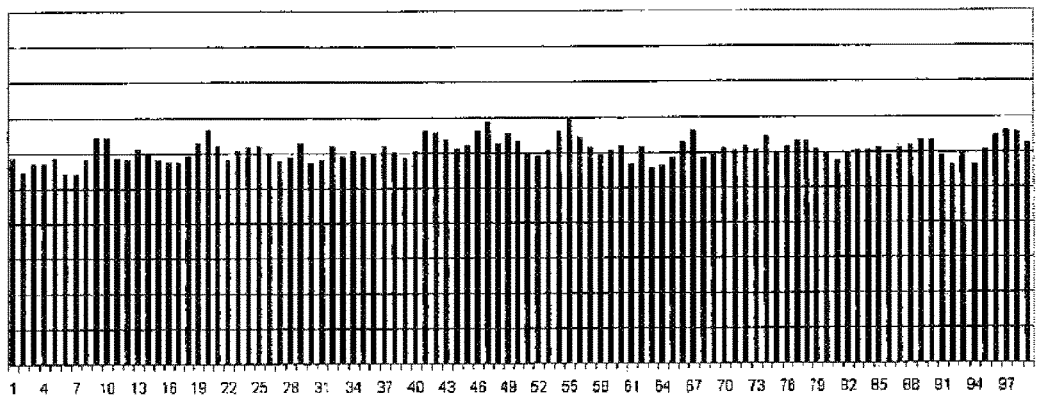
FIGS. 15 to 20 show the luminesence intensity at 1000 nm (A1, A2, A3) and 1080 nm (B1, B2, B3) at 100 respective different places of a sheet containing luminescent pigments according to the current disclosure.
Figure 16:
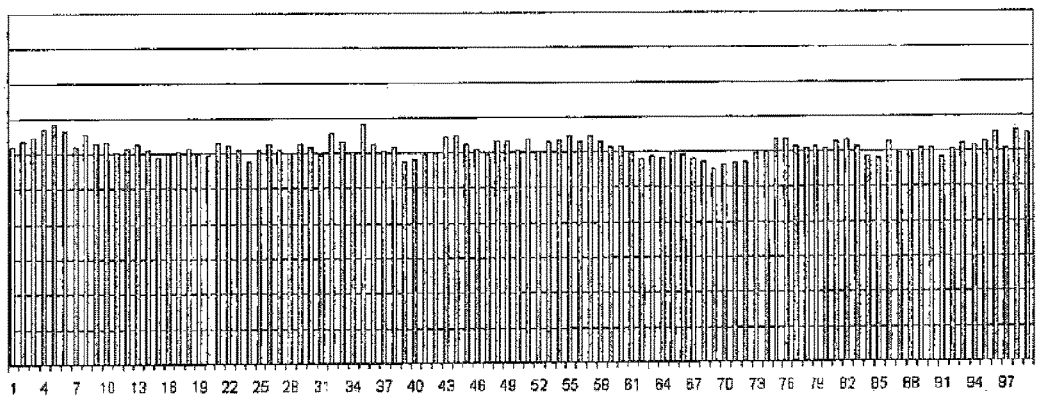
Figure 17:
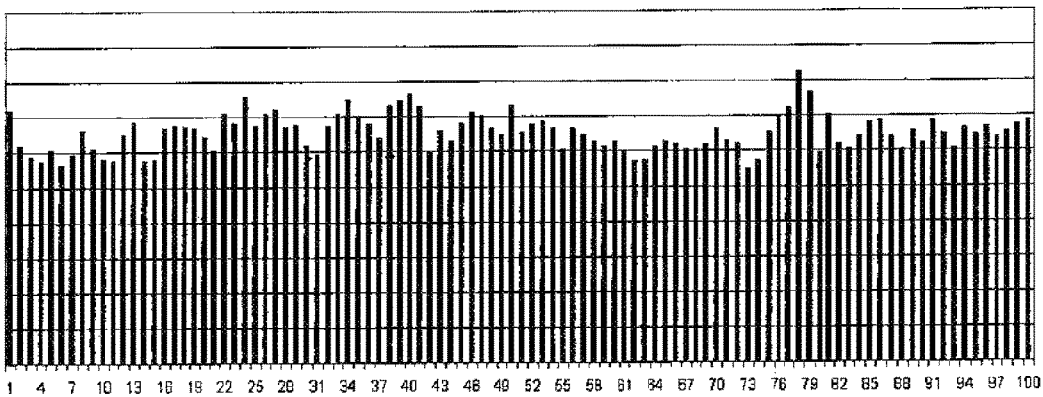
Figure 18:
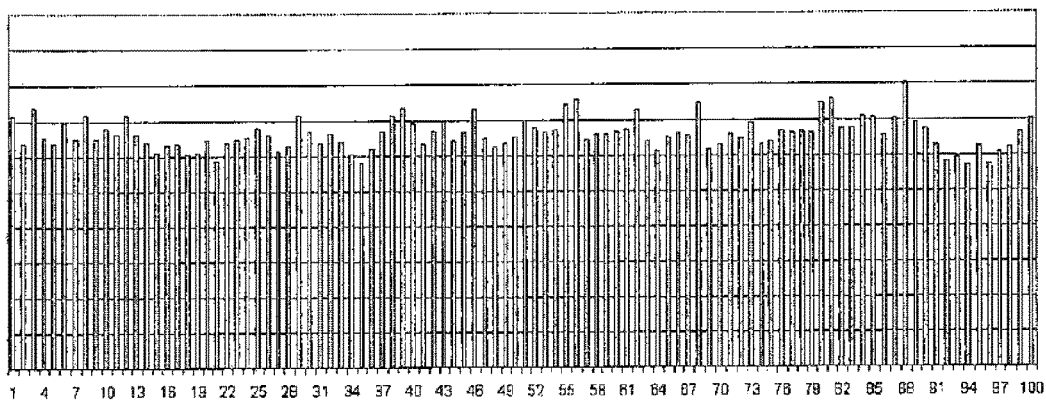
Figure 19:
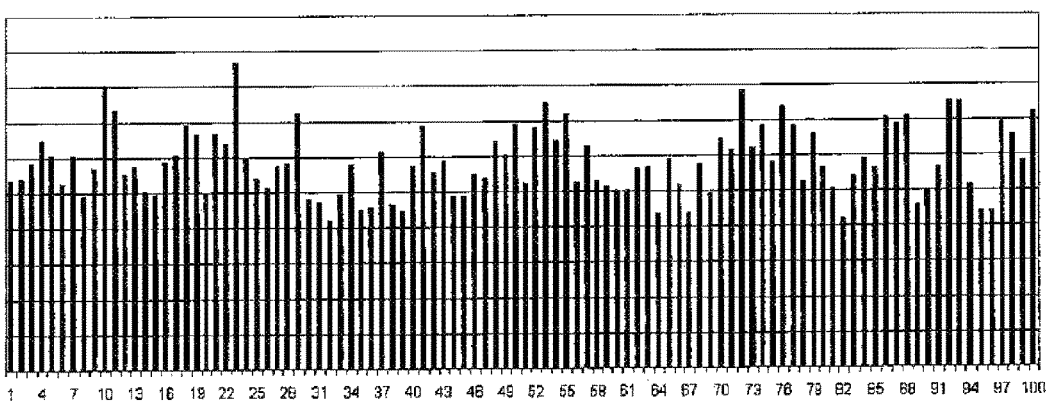
Figure 20:
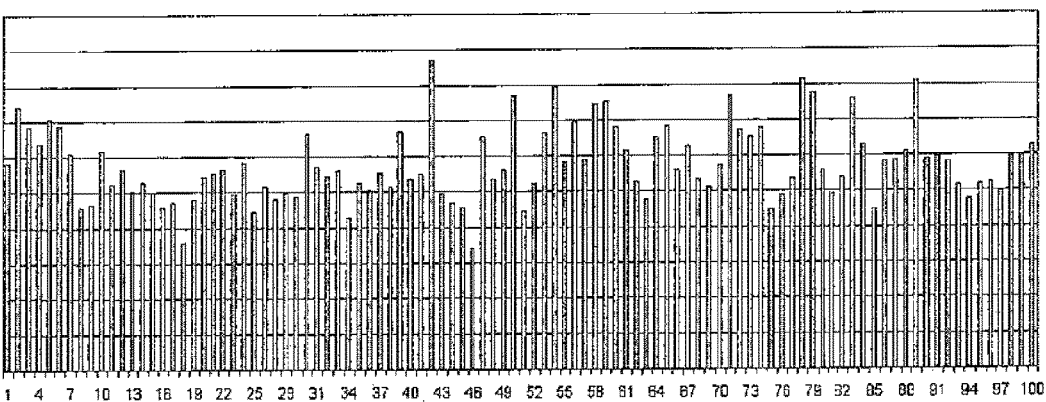

FIG. 13 shows the random distribution of luminophore particles in a 10×10 field, with the luminophore particles containing 2800 particles with a relative luminance of 1 (small boxes in FIG. 13), and 14 particles with a relative luminance of 100 (large circular spots in FIG. 13). FIG. 14 shows the resultant luminescence signal (i.e. the measured luminescence intensity) for each of the fields 1 to 10 (Y-axis) in the rows 1 to 10 (X-axis).

The completely different kind of signal fluctuation in FIG. 14 compared to the signal fluctuation in FIGS. 2, 4 and 6 can be explained by the fact that the luminescence intensity depends strongly on the particle size. Thus, a luminophore particle with a diameter of 10 µm possesses a thousand times higher volume than a luminophore particle with a diameter of only 1 µm, and an accordingly higher luminance. Additionally, energy can be emitted nonradiatively on surface defects ("surface quenching") more easily in the case of small particles, thereby further strengthening this effect.

The respectively larger particle class is thus able to clearly "outshine" the smaller particle class, thereby giving rise to characteristic, strong increases to high signal values (so-called "outliers" or "outlier signals") at measurement sites containing such particles. This gives rise to a fluctuation pattern with interspersed strong peaks which clearly differs from that of a substance with unimodal particle size distribution. Both the height and the frequency of these stronger signals can be evaluated. With suitable mathematical methods it is also possible to identify those characteristic fluctuation patterns caused by bimodal or multimodal grain sizes that do not contain any strong "outliers". For even when the grain sizes of the smaller and larger particle classes are not far enough apart to cause clear "outliers", the statistical parameters of such fluctuation patterns can differ clearly from those of a fluctuation pattern caused by unimodal grain size distributions.

To obtain reproducible and unambiguously distinguishable intensity distribution patterns, it is advantageous to tailor the grain size distribution of the starting materials in order to obtain e.g. a low size distribution width and an absence of fines fractions in the case of unimodal distributions of large particles, or to obtain a suitable distance of the individual modes in the case of bimodal distributions.

Classically, luminophore particles are crushed after solid synthesis by means of mills, e.g. pin mills or agitator ball mills, until the grain size desired for the application is reached. Bimodal distributions or relatively narrow distributions of "large" particles (e.g. in a range of 10 to 20 µm) can typically not be obtained. It is possible, by classical crushing techniques, such as e.g. solids grinding, to produce different grain size distributions that can be mutually distinguished by their fluctuation behavior, by varying the grinding duration or the manner of grinding. However, the grain size distributions can be optimized by additional methods. Furthermore, it is also possible to obtain grain size distributions that are otherwise unusual for security features based on luminophores.

Thus, it is possible e.g. to produce larger particle units again through a controlled agglomeration of fine material obtained by means of grinding. By a choice of suitable agglomeration techniques there can be obtained unimodal grain size distributions in a range of 10 µm to 20 µm. This size range is difficult to obtain by means of classical synthesis techniques, such as oven annealing, since either crystallites that are too small are produced, or particles that are too large and in turn produce smaller fragments during the grinding process, thus leading to a wide grain size distribution.

Due to the clear difference in size distribution, such agglomerates are suited to some extent for producing bimodal distributions, namely by combination with ground material with grain sizes in a range of 1 to 10 µm. It is to be noted that the use of accordingly large single crystals is preferred in certain cases. Through the effect of surface quenching, the luminescence intensity is clearly reduced in comparison to a single crystal, depending on the size of the smaller particles composing the agglomerate. Thus, clear differences in the fluctuation behavior can arise here even with apparently the same grain size distribution.

It is hence particularly preferred to choose synthesis conditions in which bimodal products can be obtained e.g. via Ostwald ripening without additional grinding steps. Alternatively, the synthesis conditions are optimized with regard to the growth of large crystals, which are then mixed in a suitable ratio with separately synthesized, smaller crystals or ground material. In some cases a suitable bimodal distribution can also be produced by mixing very differently ground material. However, it might be necessary here to further adapt the grain size distributions, e.g. via dry screening or sedimentation separation. The above-mentioned production of agglomerates from fine material is preferred over the addition of larger crystallites only in the case of those host lattices with which the synthesis of larger crystallites is unreasonably elaborate.

Figure 26:
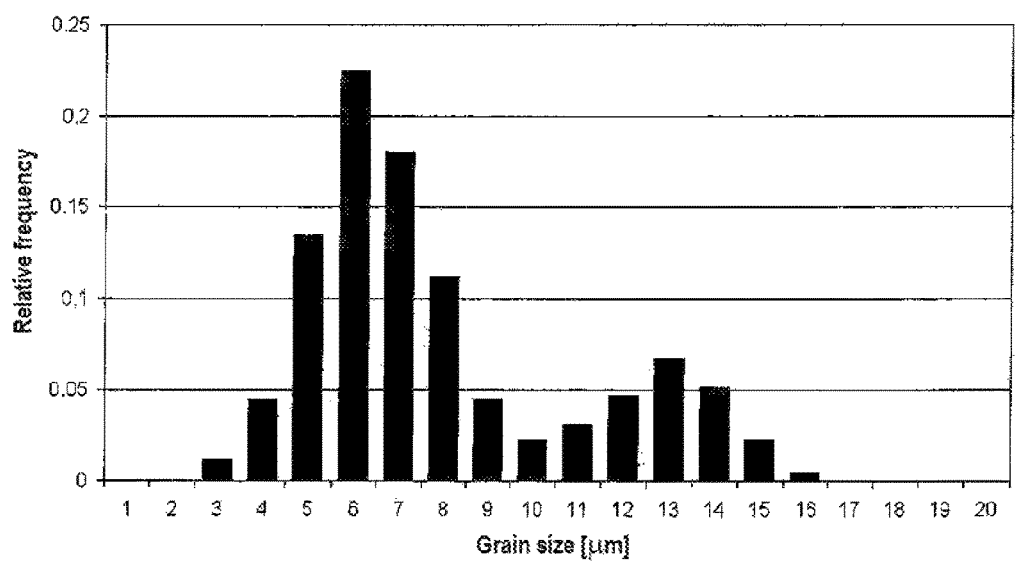
FIG. 26 shows a schematic grain size histogram (i.e. the plot of relative frequency as a function of grain size) for an arbitrarily chosen bimodal distribution.

In addition to the embodiment described with reference to FIGS. 13 and 14, FIG. 26 shows a schematic grain size histogram (i.e. the plot of relative frequency as a function of grain size) for an arbitrarily chosen bimodal distribution. The distribution shown in FIG. 26 has an overlap of the two peaks or maxima. However, a clearly stronger overlap, or no overlap, of the two peaks is also possible in principle.

Figure 27:
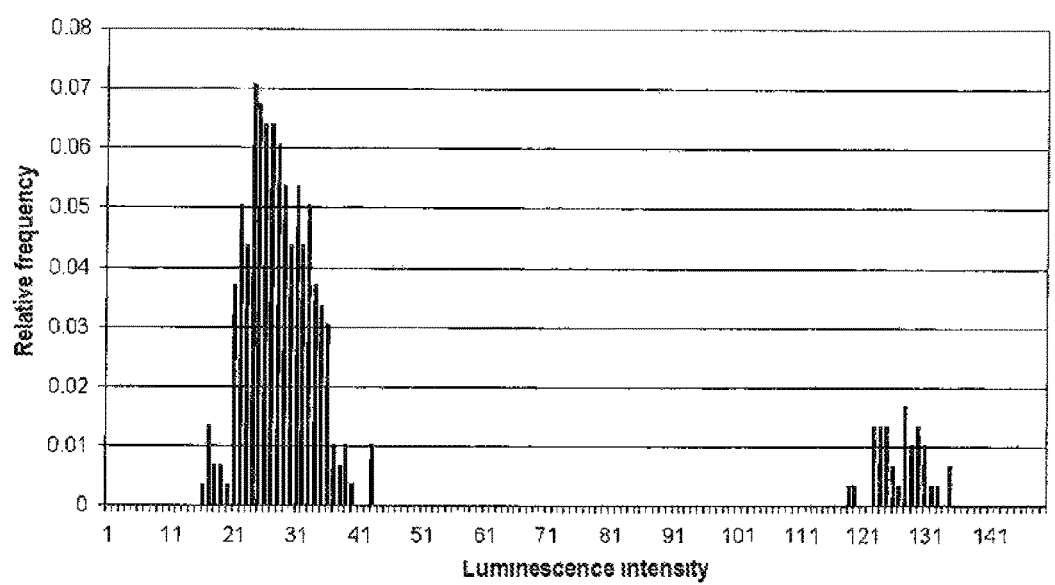
FIG. 27 shows a hypothetical histogram of the luminescence intensities of 250 measurement points undre the same conditions as those of the model of FIGS. 13 and 14.

FIG. 27 shows a hypothetical histogram of the luminescence intensities of 250 measurement points under the same conditions as those of the model of FIGS. 13 and 14.

Third Preferred Embodiment

The third preferred embodiment is based on mixing different luminescence particles with different luminescence wavelength (see the following exemplary embodiment).

<General Formula 1 for Producing a Luminescence Particle Agglomerate>

10 g of NIR luminescent pigment is dispersed in 60 g of water. 120 ml of ethanol and 3.5 ml of ammonia (25%) are added. 10 ml of tetraethyl orthosilicate is added with stirring, and the reaction mixture stirred for 8 more hours.

The product is filtered off, washed twice with 40 ml of water and dried at 60° C. in a drying oven. Particle agglomerates with a grain size D99=20-30 µm are obtained.

The obtained agglomerates are tempered for 1 hour at 300° C. and subsequently treated with an ultra centrifugal mill. There is obtained a product with a reduced grain size of D99=15-18 µm <General Formula 2 for Producing a Luminescence Particle Agglomerate>

33 g of NIR luminescent pigment is dispersed in 245 g of water. 44 g of potassium hydrogencarbonate is added, and a potassium water glass solution in drops with stirring in the course of one hour, so that at the end a $SiO_2$ content of approx. 20% is present in the product.

The product is filtered off, washed twice with 150 ml of water and dried at 60° C. in a drying oven. There are obtained particle agglomerates with a grain size D99=18-20 µm.

Exemplary Embodiment 2

Starting out from an NIR luminescent pigment (emission at 1000 nm) with an average grain size (A2), a finer pigment (A1) is produced by grinding in an agitator ball mill, and a coarser pigment (A3) by controlled agglomeration according to formula 2 (see Table 2).

By identical treatment of a second NIR luminescent pigment which differs from the first NIR luminescent pigment in the wavelength of the emission (1082 nm), the analogous pigments B1, B2 and B3 are produced.

TABLE 2

| Designation | Grain sizes of the pigments | | |
| --- | --- | --- | --- |
| | D50 [µm] | D90 [µm] | D99 [µm] |
| A1/B1 | 0.3 | 1.4 | 2.2 |
| A2/B2 | 2.4 | 7 | 11.4 |
| A3/B3 | 11 | 16 | 20 |

Subsequently, paper sheets with different combinations of an A pigment and a B pigment are produced in a sheet former. The luminescent pigments are used here in suitable concentrations, typically 0.1 percent by weight for the pigments A2, B2, A3 and B3, so that an, on average, equally strong luminescence intensity is obtained in all sheets. The pigments A1 and B1 are metered accordingly higher, e.g. with 0.2 percent by weight, to compensate their luminescence intensity being reduced due to the small grain size.

The luminescence intensity of the A pigment and of the B pigment at their respective emission wavelengths is subsequently measured at a plurality of different places (size of the measurement spot<1 mm$^2$) of the sheet (see FIGS. 15 to 20).

FIGS. 15 to 20 show the luminescence intensity at 1000 nm (A1, A2, A3) and 1080 nm (B1, B2, B3) at 100 respective different places of a sheet containing the corresponding luminescent pigments.

With reference to FIGS. 15 to 20, a clear influence of the grain size on the spatial homogeneity of the signal intensity can be recognized. Mathematically, this state of affairs can be stated for example by stating the standard deviation of the luminescence intensity at 100 different measurement points. It lies typically in the range of 25 to 35 for the pigments A1 and B1 with low grain size, typically in the range of 45 to 55 for the pigments A2 and B2 with average grain size, and typically in the range of 95 to 105 for the pigments A3 and B3 with large grain size. The mean of the luminescence intensity lies at about 600 arbitrarily selected units for all sheets used in the examples.

Assuming that the combination of the luminescent pigments A and B is a luminescent substance coding used for safeguarding a value document, the number of possible codings can be increased by a factor of 9 by including the range of variation as a safeguarding criterion. Through skillful manipulation of the grain size distribution of the luminescent pigments used, the nine combinations A1+B1, A1+B2, A1+B3, A2+B1, A2+B2, A2+B3, A3+B1, A3+B2, A3+B3 are mutually distinguishable, although the pigment types used are respectively identical spectrally.

The following description contains preferred embodiments with regard to the evaluation of the luminescence fluctuation in general.

In principle, the fluctuation of a feature can be analyzed absolutely, relatively to itself, or relatively to the fluctuation of another feature.

"Absolute" is understood herein to mean that it is checked e.g. whether the average deviation from the signal mean exceeds or undershoots a certain absolute value, or whether the "outlier signals" arising from a bimodal distribution with high differences in size lie within a certain values range of the signal intensity. Likewise, it can be analyzed whether the percentage number of measurement sites with a specific property, e.g. the exceeding of a certain threshold value, lies within a specified range.

The designation "relatively to itself" designates herein methods in which no absolute values are checked, but rather in which it is checked for example whether the average deviation relative to the average of the feature intensity lies within or outside a certain percentage.

However, for many applications the third method, measurement of the fluctuation "relatively to another feature", is especially advantageous. In particular those cases should be mentioned here in which foreign effects, such as an overprinting of the bank note or a watermark (i.e. a local change of thickness or density in the paper substrate), spuriously affect the measurements. Thus, e.g. overprinting with a stripe pattern which partly absorbs the excitation wavelength causes a fluctuation of the feature signal which does not arise from the nature of the feature alone (see FIG. 21).

Figure 21:
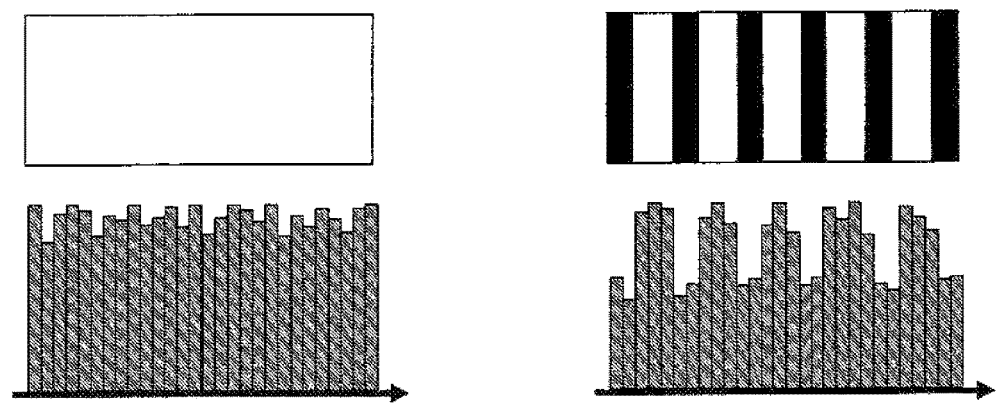
FIG. 21 shows the luminescence fluctuation caused by overprinting with a stripe pattern.

FIG. 21 shows the luminescence fluctuation caused by overprinting with a stripe pattern.

If, however, there is added a second feature whose fluctuation is influenced by the stripe pattern in a similar way, the spurious effect can be compensated by comparison of the two signals. Thus, it is possible e.g. to add a "normalizing substance" with a spatially especially homogeneous signal, whose signal fluctuation is thus determined almost exclusively by external factors, such as the overprinting. By correction of a feature signal by the signal of the normalizing substance as measured at the measurement site, said external factors are thus "stripped out" (FIG. 22).

Figure 22:
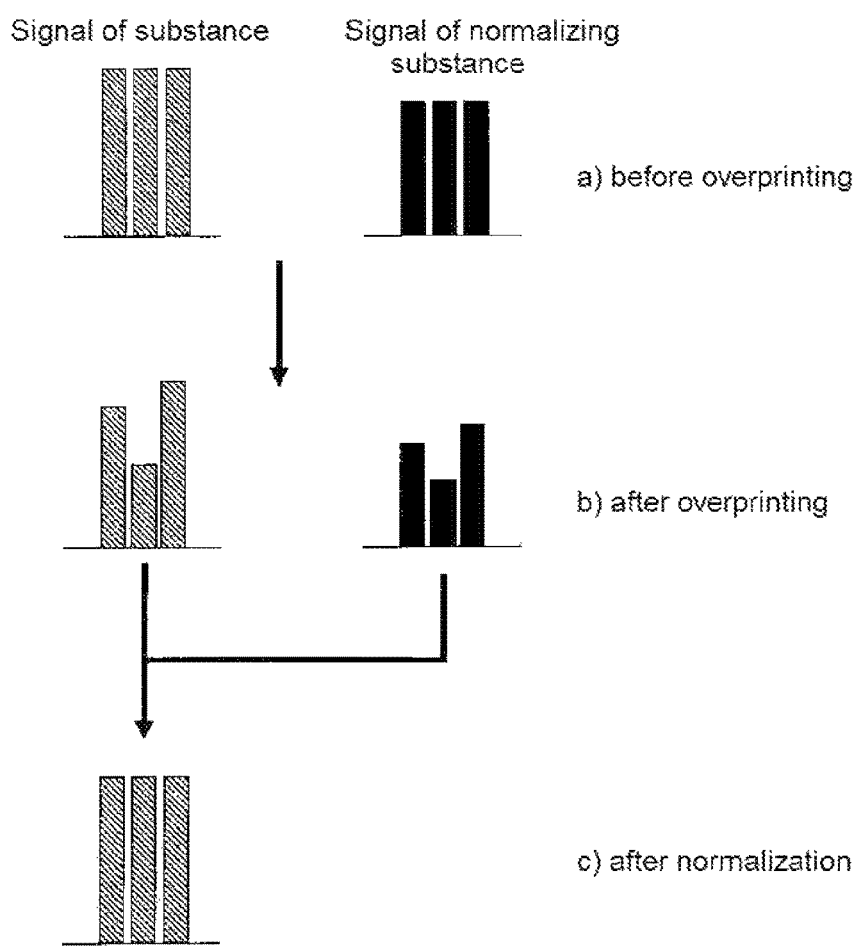
FIG. 22 shows the elimination of overprinting effects by the addition of a normalizing component.

FIG. 22 shows the elimination of overprinting effects by the addition of a normalizing component.

The method is not only limited to the embodiment of such a "homogeneous-signal normalizing substance". Thus, it is e.g. also possible to compare the relative extent of the fluctuation of two substances with each other. To explain these relations it is expedient to use a representation in the form of point clouds (see FIG. 23). The position of the cloud center gives information about the average signal intensities, and the extension of the cloud indicates the extent of signal fluctuation.

Figure 23:
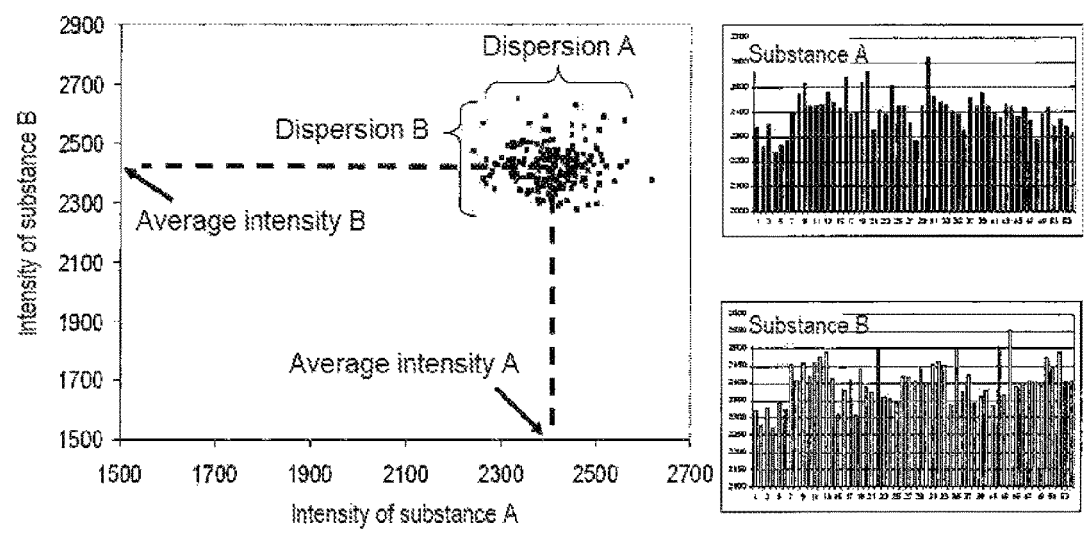
FIG. 23 shows a point cloud representation of the signal intensities of two features at the same respective measurement site.

FIG. 23 shows a point cloud representation of the signal intensities of two features at the same respective measurement site.

Figure 24:
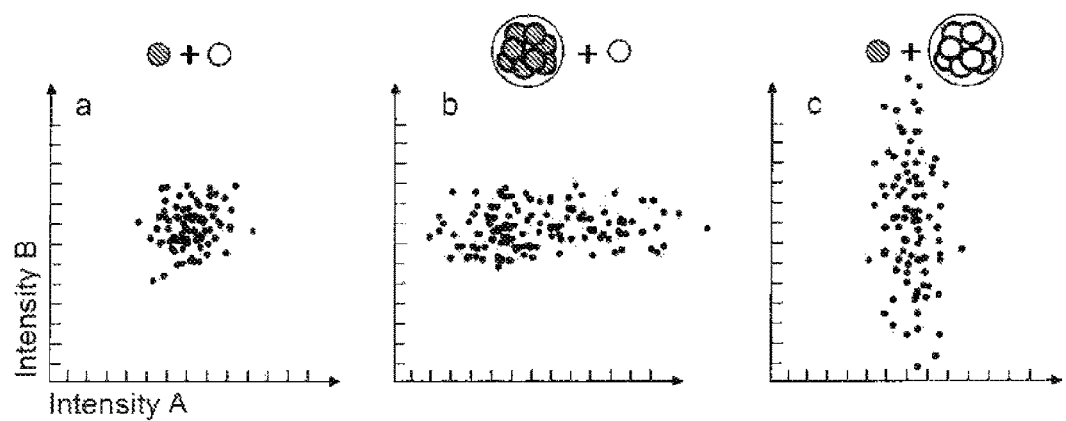
FIG. 24 shows point couds for different combinations of fine and coarse luminophores.

As an example of application, FIG. 24 shows different combinations of fine and coarse particles of two luminophores in a respective sheet. The "coarse" luminophore particles consist respectively of silica-encapsulated agglomerates of the "fine" luminophores. It is clearly recognizable that the agglomerates fluctuate more strongly (wider point clouds).

FIG. 24 shows point clouds for different combinations of fine and coarse luminophores.

Figure 25:
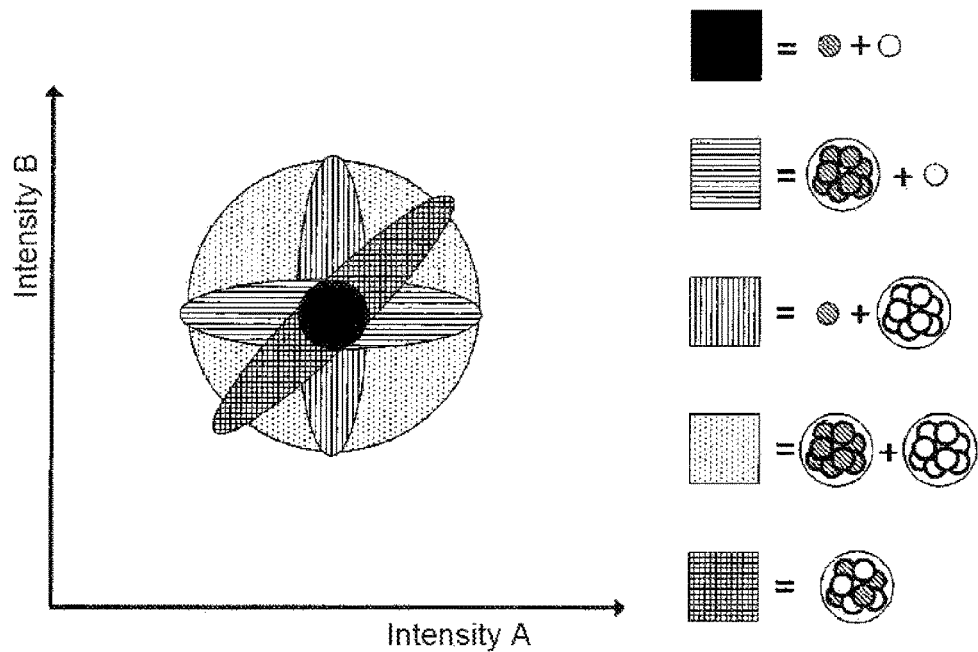
FIG. 25 shows idealied point clouds of further combinations of substances.

Idealized point clouds of further combinations of substances are depicted in FIG. 25. It can be clearly recognized that the point clouds of different combinations differ strongly e.g. in their length-to-width ratio or in their extension. The extension of such point clouds can e.g. be captured mathematically via the distances of suitable quantiles, to thereby compare the fluctuation of the two features relatively to each other and to mutually distinguish different codings.

An evaluation is of course also possible by combination of the check of absolute and relative limiting values, as well as through a combination of the individual consideration of the feature and comparison with one (or more) additional component(s).

Likewise, not all evaluation methods are equally well suited for all possibilities of combination. In the case of strongly bimodal distributions, for example, it is usually unnecessary to take account of overprinting effects, etc., since the signal differences between small and large particles are large enough to nevertheless be unambiguously distinguishable from a unimodal distribution. A comparison with e.g. a second feature component is not compulsory in this case.

In principle, the luminescent substances used according to the invention can be incorporated in the value document itself, in particular in the paper substrate. Additionally or alternatively, the luminescent substances can be applied on the value document (e.g. the luminescent substances can be imprinted on the paper substrate). The value-document substrate need not necessarily be a paper substrate, but might also be a plastic substrate or a substrate having both paper constituents and plastic constituents.

The above exemplary embodiments are based on luminescent feature substances. Instead of luminescent feature substances, use can also be made of non-luminescent feature substances that are detectable in particular by means of nuclear resonance spectroscopy, electron spin resonance spectroscopy, nuclear quadrupole resonance spectroscopy, SER (surface enhanced Raman) spectroscopy or SEIRA (surface enhanced infrared absorption) spectroscopy.

Summary of the Preferred Embodiments

1. A method for checking, in particular the authenticity and/or the nominal value of, a value document having luminescent feature substances, comprising:

a1) the step of carrying out a location-specific measurement of first luminescence intensities (L1) at a first emission wavelength at different locations of the value document that have the location coordinates (O), to thereby obtain (O/L1) measurement value pairs;

b1) the step of statistically analyzing the first luminescence intensities (L1) measured in dependence on the individual location coordinates (O), by determining at least one statistical parameter using a statistical method; and c1) the step of comparing the statistical parameter determined in the step b1) with one or more threshold values or limiting values.

The step c1) is in particular the step of checking whether the statistical parameter determined in the step b1) lies above or below a certain limiting value, or whether the statistical parameter determined in the step b1) lies within a range that is formed by a lower limiting value and an upper limiting value.

2. The method according to item 1, wherein the method has in addition to the substeps a1), b1) and c1) the following substeps a2), b2) and c2):

a2) the step of carrying out a location-specific measurement of second luminescence intensities (L2) at a second emission wavelength at the different locations of the value document that have the location coordinates (O), to thereby obtain (O/L2) measurement value pairs;

b2) the step of statistically analyzing the second luminescence intensities (L2) measured in dependence on the individual location coordinates (O), by determining at least one statistical parameter using a statistical method; and c2) the step of comparing the statistical parameter determined in the step b2) with one or more threshold values.

The step c2) is in particular the step of checking whether the statistical parameter determined in the step b2) lies above or below a certain limiting value, or whether the statistical parameter determined in the step b2) lies within a range that is formed by a lower limiting value and an upper limiting value.

3. The method according to item 1 or 2, wherein the statistical method and the statistical parameter are chosen from the methods and parameters of the field of descriptive statistics or numerical classification methods, with the field of descriptive statistics being preferred and therein in particular the field of dispersion measures being preferred, and with the field of numerical classification methods being likewise preferred and therein in particular an application to frequency distribution data and/or frequency domains being preferred.

4. The method according to item 1, wherein at least 20, preferably at least 40, particularly preferably at least 100, (O/L1) measurement value pairs are evaluated per value document for determining the statistical parameter.

5. The method according to item 2, wherein the method has additional substeps a), b) and c) which are defined analogously to the substeps a2), b2) and c2), in which the carrying out of the measurement and analyzing of the measuring data obtained therefrom is effected on the basis of further emission wavelengths in addition to the first and second emission wavelengths, e.g. on the basis of a third emission wavelength.

6. The method according to any of items 1 to 5, wherein the luminescence intensities drawn on for the statistically analyzing step are respectively corrected luminescence intensities converted by means of an algorithm.

7. The method according to item 6, wherein the value document has an additional, luminescent feature substance suitable as a normalizing substance, so that effects influencing the measurement of the luminescence intensities, such as e.g. an attenuation of measured luminescence intensities through partial overprinting of the value document, are correctable on the basis of the measured luminescence intensity of the normalizing substance.

8. The method according to any of items 1 to 7, wherein the luminescence intensities stated in the step b1) form a unimodal frequency distribution, i.e. in a histogram plotting relative frequency as a function of intensity the frequency distribution has the form of an individual peak with exactly one maximum.

9. The method according to any of items 1 to 7, wherein the luminescence intensities stated in the step b1) form a bimodal frequency distribution, i.e. in a histogram plotting relative frequency as a function of intensity the frequency distribution has the form of altogether two peaks with exactly two maxima.

10. The method according to any of items 1 to 7, wherein:
the luminescence intensities stated in the step b1) form a multimodal frequency distribution, i.e. in a histogram plotting relative frequency as a function of intensity the frequency distribution has the form of a plurality (n) of peaks with exactly (n) maxima, where n≥3.

11. A value document which is adapted to the method for checking, in particular its authenticity and/or its nominal value, according to item 1 or 8, wherein:
the value document has first luminescent particles which emit at a first emission wavelength;
the first luminescent particles are present in the value document in homogeneous distribution;
the first luminescent particles are formed with unimodal size distribution, i.e. with a certain size; and
the first luminescent particles are in particular luminescent, particulate agglomerates of a solid homogeneous phase of a luminophore.

12. A value document which is adapted to the method for checking, in particular its authenticity and/or its nominal value, according to item 1 or 2, wherein:
the value document has first luminescent particles which emit at a first emission wavelength, and second luminescent particles which emit at a second emission wavelength;

the first and the second luminescent particles are respectively present in the value document in homogeneous distribution;

the first and the second luminescent particles are respectively formed with unimodal size distribution, i.e. with a certain size; and the first and/or second luminescent particles are in particular luminescent, particulate agglomerates of a solid homogeneous phase of a luminophore.

13. The value document according to item 12, wherein the first luminescent particles possess a similar grain size to the second luminescent particles, with the grain size (D99) of the first and second particles deviating from each other by less than 50%, preferably by less than 30%.

14. The value document according to item 12, wherein the grain size (D99) of the second luminescent particles is one and a half to 50 times, preferably 2 to 20 times, particularly preferably 4 to 10 times, greater than the grain size of the first luminescent particles.

15. A value document which is adapted to the method for checking, in particular its authenticity and/or its nominal value, according to item 1 or 9, wherein:

the value document has first luminescent particles which emit at a first emission wavelength;

the first luminescent particles are formed with bimodal size distribution, i.e. with two mutually delimited, certain sizes; and the first luminescent particles are present in the value document in homogeneous distribution.

16. A value document which is adapted to the method for checking, in particular its authenticity and/or its nominal value, according to item 1 or 2, wherein:

the value document has first luminescent particles which emit at a first emission wavelength, and second luminescent particles which emit at a second emission wavelength;

the first and the second luminescent particles are respectively present in the value document in homogeneous distribution; and the first luminescent particles are formed with bimodal size distribution, i.e. with two mutually delimited, certain sizes; and the second luminescent particles have a unimodal, bimodal, or multimodal size distribution.

17. The value document according to item 15 or 16, wherein the bimodal size distribution in the histogram is so configured that one maximum is one and a half to 50 times, preferably 2 to 20 times, particularly preferably 4 to 10 times, greater with regard to its grain size than the other maximum.

18. The value document according to any of items 15 to 17, wherein at least a bimodal size distribution is produced by a mixture of smaller particles and larger single crystals.

19. The value document according to any of items 15 to 17, wherein at least a bimodal size distribution is produced by a mixture of smaller particles and larger particles, and the larger particles are luminescent, particulate agglomerates of a solid homogeneous phase of a luminophore.

20. A value document which is adapted to the method for checking, in particular its authenticity and/or its nominal value, according to item 1 or 10, wherein:

the value document has first luminescent particles which emit at a first emission wavelength;

the first luminescent particles are formed with multimodal size distribution, i.e. with at least three mutually delimited, certain sizes; and the first luminescent particles are present in the value document in homogeneous distribution.

21. A value document which is adapted to the method for checking, in particular its authenticity and/or its nominal value, according to item 1 or 2, wherein:

the value document has first luminescent particles which emit at a first emission wavelength, and second luminescent particles which emit at a second emission wavelength;

the first and the second luminescent particles are respectively present in the value document in homogeneous distribution; and the first luminescent particles are formed with multimodal size distribution, i.e. with at least three mutually delimited, certain sizes; and the second luminescent particles have a unimodal, bimodal, or multimodal size distribution.

22. The value document according to any of items 11 to 21, wherein the grain size (D99) of the luminescent particles is smaller than 30 µm, preferably smaller than 20 µm.

23. Use of the value document according to item 11 in the method according to item 1 or 8.

24. Use of the value document according to any of items 12 to 14 in the method according to item 2.

25. Use of the value document according to item 15 in the method according to item 1 or 9.

26. Use of the value document according to any of items 16 to 19 in the method according to item 2.

27. Use of the value document according to item 20 in the method according to item 1 or 10.

28. Use of the value document according to item 21 in the method according to item 2.

29. A value-document system, comprising value documents with a first nominal value or a first currency (so-called first group of value documents), value documents with a second nominal value or a second currency (so-called second group of value documents) and value documents with a third nominal value or a third currency (so-called third group of value documents), wherein at least two of the three groups of value documents are chosen from the following three kinds of value documents, and preferably all three groups of value documents are represented by the following three kinds of value documents:

first value documents which are respectively defined according to item 11, wherein each value document possesses the luminescent particles in a certain grain size;

second value documents which are respectively defined according to item 11, wherein each value document possesses the luminescent particles in a lower grain size than the grain size of the luminescent particles of the first value documents; and third value documents which are respectively defined according to item 11, wherein each value document possesses the luminescent particles in a greater grain size than the grain size of the luminescent particles of the first value documents.

30. The value-document system according to item 29, wherein the concentration of the luminescent particles of the second value documents is higher than the concentration of the luminescent particles of the first value documents and/or the concentration of the luminescent particles of the third value documents is lower than the concentration of the luminescent particles of the first value documents, wherein preferably the concentrations of the luminescent particles in the second and/or third value documents are so chosen that the average luminescence intensity of the second and/or third value documents matches the average luminescence intensity of the first value documents.

31. The value-document system according to item 29 or 30, wherein the luminescent particles of the third value documents are luminescent, particulate agglomerates of a solid homogeneous phase of a luminophore.

32. The value-document system according to any of items 29 to 31, which comprises in addition to the second and/or third value documents further kinds of value documents, wherein each individual kind of value documents contains luminescent particles with lower or greater grain sizes than those of the first value documents.

33. The value-document system according to any of items 29 to 32, wherein the value documents contain in addition to the stated luminescent particles further luminophores with different spectral properties with regard to excitation wavelength and/or emission wavelength, preferably further luminescent particles with different emission wavelength.

34. A value-document system, comprising value documents with a first nominal value or a first currency (so-called group I of value documents), value documents with a second nominal value or a second currency (so-called group II of value documents), optionally value documents with a third nominal value or a third currency (so-called group III of value documents), optionally value documents with a fourth nominal value or a fourth currency (so-called group IV of value documents), optionally value documents with a fifth nominal value or a fifth currency (so-called group V of value documents), optionally value documents with a sixth nominal value or a sixth currency (so-called group VI of value documents), optionally value documents with a seventh nominal value or a seventh currency (so-called group VII of value documents), optionally value documents with an eighth nominal value or an eighth currency (so-called group VIII of value documents), and optionally value documents with a ninth nominal value or a ninth currency (so-called group IX of value documents), wherein at least one of the groups I to IX consists of the following value documents A, and at least one further one of the groups I to IX of value documents is chosen from the following kinds B to J of value documents, preferably at least one of the groups I to IX consists of the following value documents A, and two further ones of the groups I to IX of value documents are chosen from the following kinds B to J of value documents, further preferably at least one of the groups I to IX consists of the following value documents A, and three further ones of the groups I to IX of value documents are chosen from the following kinds B to J of value documents, and particularly preferably the groups I to IX of value documents are represented by the following kinds of value documents A to J:

value documents A which are respectively defined according to item 12, wherein each value document both contains the first luminescent particles in a certain grain size and contains the second luminescent particles in a certain grain size;

value documents B which are respectively defined according to item 12, wherein each value document both contains the first luminescent particles in a lower grain size than the grain size of the first luminescent particles of the value documents A and contains the second luminescent particles in a lower grain size than the grain size of the second luminescent particles of the value documents A;

value documents C which are respectively defined according to item 12, wherein each value document contains the first luminescent particles in the same grain size as the grain size of the first luminescent particles of the value documents A, and contains the second luminescent particles in a lower grain size than the grain size of the second luminescent particles of the value documents A;

value documents D which are respectively defined according to item 12, wherein each value document contains the first luminescent particles in a lower grain size than the grain size of the first luminescent particles of the value documents A and contains the second luminescent particles in the same grain size as the grain size of the second luminescent particles of the value documents A;

value documents E which are respectively defined according to item 12, wherein each value document both contains the first luminescent particles in a greater grain size than the grain size of the first luminescent particles of the value documents A and contains the second luminescent particles in a greater grain size than the grain size of the second luminescent particles of the value documents A;

value documents F which are respectively defined according to item 12, wherein each value document contains the first luminescent particles in the same grain size as the grain size of the first luminescent particles of the value documents A and contains the second luminescent particles in a greater grain size than the grain size of the second luminescent particles of the value documents A;

value documents G which are respectively defined according to item 12, wherein each value document contains the first luminescent particles in a greater grain size than the grain size of the first luminescent particles of the value documents A and contains the second luminescent particles in the same grain size as the grain size of the second luminescent particles of the value documents A;

value documents H which are respectively defined according to item 12, wherein each value document contains the first luminescent particles in a lower grain size than the grain size of the first luminescent particles of the value documents A and contains the second luminescent particles in a greater grain size than the grain size of the second luminescent particles of the value documents A;

value documents J which are respectively defined according to item 12, wherein each value document contains the first luminescent particles in a greater grain size than the grain size of the first luminescent particles of the value documents A and contains the second luminescent particles in a lower grain size than the grain size of the second luminescent particles of the value documents A.

35. The value-document system according to item 34, wherein the concentration of the respective first and/or second luminescent particles is higher in a group of value documents than the corresponding concentration of the respective first and/or second luminescent particles in value documents A when the grain size of the respective first and/or second luminescent particles is lower than the grain size of the respective first and/or second luminescent particles in value documents A, and/or the concentration of the respective first and/or second luminescent particles in a group of value documents is lower than the corresponding concentration of the respective first and/or second luminescent particles in value documents A when the grain size of the respective first and/or second luminescent particles is greater than the grain size of the respective first and/or second luminescent particles in value documents A, wherein preferably the concentration of the respective first and/or second luminescent particles is so chosen that the resultant average first and/or second luminescence intensity of the value documents containing the respective first and/or second luminescent particles matches the corresponding average first and/or second luminescence intensities of the value documents A.

36. The value-document system according to item 34 or 35, wherein in at least one group of value documents the first and/or second luminescent particles are luminescent, particulate agglomerates of a solid homogeneous phase of a luminophore.

37. The value-document system according to any of items 34 to 36, which comprises in addition to the stated value documents further value documents which contain first and/or second luminescent particles with lower and/or greater grain sizes than the value documents A.

38. The value-document system according to item 34, wherein in addition to the first and second luminescent particles, further luminophores, for example at least third luminescent particles, are contained in the value documents.

39. A value-document system, comprising value documents with a first nominal value or a first currency (so-called first group of value documents), value documents with a second nominal value or a second currency (so-called second group of value documents) and value documents with a third nominal value or a third currency (so-called third group of value documents), wherein at least two of the three groups of value documents are chosen from the following three kinds of value documents, and preferably all three groups of value documents are represented by the following three kinds of value documents:

first value documents which are respectively defined according to item 11, wherein each value document possesses the luminescent particles in a unimodal grain size distribution;

second value documents which are respectively defined according to item 15, wherein each value document possesses the luminescent particles in a bimodal grain size distribution; and third value documents which are respectively defined according to item 20, wherein each value document possesses the luminescent particles in a multimodal grain size distribution.

40. The value-document system according to item 39, wherein the concentrations of the luminescent particles in the respective first, second and third value documents are so chosen that luminescent particles with a first grain size distribution that possess a higher luminescence intensity than luminescent particles with a second grain size distribution are used in a lower concentration, wherein preferably the concentrations of the luminescent particles in the corresponding value documents are so chosen that all value documents have the same average luminescence intensity.

41. The value-document system according to item 39 or 40, wherein at least in one group of value documents the luminescent particles are formed completely or partly by luminescent, particulate agglomerates of a solid homogeneous phase of a luminophore.

42. The value-document system according to any of items 39 to 41, which comprises in addition to the stated groups of value documents further groups of value documents which are respectively chosen from first, second or third kinds of value documents, with groups of value documents of the same respective kind of value documents mutually differing in the position of at least one maximum of the grain size distribution of the contained luminescent particles.

43. The value-document system according to any of items 39 to 42, wherein the value documents contain in addition to the stated luminescent particles further luminophores with different spectral properties, preferably further luminescent particles with different emission.

44. A value-document system, comprising value documents with a first nominal value or a first currency (so-called group I of value documents), value documents with a second nominal value or a second currency (so-called group II of value documents), optionally value documents with a third nominal value or a third currency (so-called group III of value documents), optionally value documents with a fourth nominal value or a fourth currency (so-called group IV of value documents), optionally value documents with a fifth nominal value or a fifth currency (so-called group V of value documents), optionally value documents with a sixth nominal value or a sixth currency (so-called group VI of value documents), optionally value documents with a seventh nominal value or a seventh currency (so-called group VII of value documents), optionally value documents with an eighth nominal value or an eighth currency (so-called group VIII of value documents), and optionally value documents with a ninth nominal value or a ninth currency (so-called group IX of value documents), wherein at least one of the groups I to IX consists of one of the following eight kinds of value documents B to J, and at least one further one of the groups I to IX of value documents is chosen from the following nine kinds of value documents A to J, preferably at least one of the groups I to IX consists of one of the following eight kinds of value documents B to J, and two further ones of the groups I to IX of value documents are chosen from the following nine kinds of value documents A to J, further preferably at least one of the groups I to IX is chosen from one of the following eight kinds of value documents B to J, and three further ones of the groups I to IX of value documents are chosen from the following nine kinds of value documents A to J, particularly preferably the groups I to IX of value documents are represented by the following nine kinds of value documents A to J:

value documents A which are respectively defined according to item 12, wherein each value document both contains the first luminescent particles in a unimodal grain size distribution and contains the second luminescent particles in a unimodal grain size distribution;

value documents B which are respectively defined according to item 16, wherein each value document both contains the first luminescent particles in a bimodal grain size distribution and contains the second luminescent particles in a bimodal grain size distribution;

value documents C which are respectively defined according to item 16, wherein each value document contains the first luminescent particles in a unimodal grain size distribution and contains the second luminescent particles in a bimodal grain size distribution;

value documents D which are respectively defined according to item 16, wherein each value document contains the first luminescent particles in a bimodal grain size distribution and contains the second luminescent particles in a unimodal grain size distribution;

value documents E which are respectively defined according to item 21, wherein each value document contains the first luminescent particles in a multimodal grain size distribution and contains the second luminescent particles in a multimodal grain size distribution;

value documents F which are respectively defined according to item 21, wherein each value document contains the first luminescent particles in a unimodal grain size distribution and contains the second luminescent particles in a multimodal grain size distribution;

value documents G which are respectively defined according to item 21, wherein each value document contains the first luminescent particles in a multimodal grain size distribution and contains the second luminescent particles in a unimodal grain size distribution;

value documents H which are respectively defined according to item 16, wherein each value document contains the first luminescent particles in a bimodal grain size distribution and contains the second luminescent particles in a multimodal grain size distribution;

value documents J which are respectively defined according to item 21, wherein each value document contains the first luminescent particles in a multimodal grain size distribution and contains the second luminescent particles in a bimodal grain size distribution.

45. The value-document system according to item 44, wherein the concentration of the respective first and/or second luminescent particles in a value document is so chosen that luminescent particles with a first grain size distribution that possess a higher luminescence intensity than luminescent particles with a second grain size distribution are used in a lower concentration, wherein preferably the concentration of the respective first and/or second luminescent particles is so chosen that the resultant average first and/or second luminescence intensity of the value documents containing the respective first and/or second luminescent particles matches the corresponding average first and/or second luminescence intensities of the value documents A.

46. The value-document system according to item 44 or 45, wherein at least in one of the groups of value documents the luminescent particles are formed completely or partly by luminescent, particulate agglomerates of a solid homogeneous phase of a luminophore.

47. The value-document system according to any of items 44 to 46, which comprises in addition to the stated groups of value documents further groups of value documents which are respectively chosen from the kinds of value documents A to J, with groups of value documents of the same respective kind of value documents mutually differing in the position of at least one maximum of the grain size distribution of the contained luminescent particles.

48. The value-document system according to item 44, wherein in addition to the first and second luminescent particles, further luminophores, for example at least third luminescent particles, are contained in the value documents.

The invention claimed is:

1. A value document wherein:
   the value document has first luminescent particles which emit at a first emission wavelength;
   the first luminescent particles having at least two mutually delimited, certain sizes; and
   the first luminescent particles are present in the value document in homogeneous spatial distribution;
wherein the at least two mutually delimited, certain sizes are produced by a mixture of smaller particles and larger single crystals, or are produced by a mixture of smaller particles and larger particles, and the larger particles are luminescent, particulate agglomerates of a solid homogeneous phase of a luminophore, and
wherein at least a part of the first luminescent particles are overprinted.

2. The value document according to claim 1, wherein the at least two mutually delimited, certain sizes of the first luminescent particles are configured to form a bimodal size distribution in a histogram plotting grain size distribution, wherein one maximum is one and a half to 50 times greater with regard to its grain size than the other maximum.

3. The value document according to claim 1, wherein the grain size (D99) of the luminescent particles is smaller than 30 µm.

* * * * *